US007972359B2

(12) United States Patent
Kreidler

(10) Patent No.: US 7,972,359 B2
(45) Date of Patent: Jul. 5, 2011

(54) INTRACARDIAC CAGE AND METHOD OF DELIVERING SAME

(75) Inventor: Marc S. Kreidler, Sunnyvale, CA (US)

(73) Assignee: Atritech, Inc., Plymouth, MN (US)

( * ) Notice: Subject to any disclaimer, the term of this patent is extended or adjusted under 35 U.S.C. 154(b) by 891 days.

(21) Appl. No.: 11/229,313

(22) Filed: Sep. 16, 2005

(65) Prior Publication Data

US 2007/0066993 A1 Mar. 22, 2007

(51) Int. Cl.
*A61B 17/08* (2006.01)
(52) U.S. Cl. .......................................... 606/213; 606/200
(58) Field of Classification Search .................. 606/213, 606/215, 151, 153, 139, 200, 191; 128/898; 604/500, 508, 284
See application file for complete search history.

(56) References Cited

U.S. PATENT DOCUMENTS

| 178,283 | A | 6/1876 | French |
| 1,967,318 | A | 7/1934 | Monahan |
| 3,402,710 | A | 9/1968 | Paleschuck |
| 3,540,431 | A | 11/1970 | Mobin-Uddin |
| 3,557,794 | A | 1/1971 | Van Patten |
| 3,638,652 | A | 2/1972 | Kelley |
| 3,811,449 | A | 5/1974 | Gravlee et al. |
| 3,844,302 | A | 10/1974 | Klein |
| 3,874,388 | A | 4/1975 | King et al. |
| 4,007,743 | A | 2/1977 | Blake |
| 4,175,545 | A | 11/1979 | Termanini |
| 4,309,776 | A | 1/1982 | Berguer |
| 4,341,218 | A | 7/1982 | U |
| 4,585,000 | A | 4/1986 | Hershenson |
| 4,603,693 | A | 8/1986 | Conta et al. |
| 4,611,594 | A | 9/1986 | Grayhack et al. |
| 4,619,246 | A | 10/1986 | Molgaard-Nielsen et al. |
| 4,638,803 | A | 1/1987 | Rand |
| 4,665,906 | A | 5/1987 | Jervis |
| 4,681,588 | A | 7/1987 | Ketharanathan |
| 4,710,192 | A | 12/1987 | Liotta et al. |
| 4,718,417 | A | 1/1988 | Kittrell et al. |
| 4,759,348 | A | 7/1988 | Cawood |

(Continued)

FOREIGN PATENT DOCUMENTS

WO WO 93/13712 7/1993

(Continued)

*Primary Examiner* — Anhtuan T Nguyen
*Assistant Examiner* — Julie A Szpira
(74) *Attorney, Agent, or Firm* — Seager, Tufte & Wickhem LLC

(57) ABSTRACT

A method of preventing ingress of material into the left atrium of a heart includes providing a delivery sheath, advancing the sheath distal end through an opening between the right atrium and the left atrium of the heart, providing an expandable cage, delivering the expandable cage to the left atrium, and expanding the expandable cage within the left atrium. The expandable cage includes a proximal end, a distal end, and a plurality of supports extending therebetween. The expandable cage also includes a first membrane provided at its proximal end and a second membrane provided at its distal end. The expandable cage has a collapsed configuration so that it can be received within the lumen of the delivery sheath, and an expanded configuration for deployment within the heart. When expanded, the first membrane is positioned at an opening between the left and right atria of the heart, and the second membrane is positioned at the ostium of the left atrial appendage. The first membrane substantially prevents passage of blood between the atria and the second membrane prevents passage of embolic material from the left atrial appendage into the left atrium of the heart.

13 Claims, 25 Drawing Sheets

U.S. PATENT DOCUMENTS

| | | |
|---|---|---|
| 4,793,348 A | 12/1988 | Palmaz |
| 4,827,907 A | 5/1989 | Tashiro |
| 4,832,055 A | 5/1989 | Palestrant |
| 4,917,089 A | 4/1990 | Sideris |
| 4,921,484 A | 5/1990 | Hillstead |
| 4,960,412 A | 10/1990 | Fink |
| 4,998,972 A | 3/1991 | Chin et al. |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,418 A | 4/1992 | Lefebvre |
| 5,108,420 A | 4/1992 | Marks |
| 5,108,474 A | 4/1992 | Riedy et al. |
| 5,116,360 A | 5/1992 | Pinchuk et al. |
| 5,122,136 A | 6/1992 | Guglielmi et al. |
| 5,171,259 A | 12/1992 | Inoue |
| 5,176,692 A | 1/1993 | Wilk et al. |
| 5,192,301 A | 3/1993 | Kamiya et al. |
| 5,211,658 A | 5/1993 | Clouse |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,284,488 A | 2/1994 | Sideris |
| 5,304,184 A | 4/1994 | Hathaway et al. |
| 5,306,234 A | 4/1994 | Johnson |
| 5,312,341 A | 5/1994 | Turi |
| 5,334,217 A | 8/1994 | Das |
| 5,344,439 A | 9/1994 | Otten |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,375,612 A | 12/1994 | Cottenceau et al. |
| 5,397,355 A | 3/1995 | Marin et al. |
| 5,417,699 A | 5/1995 | Klein et al. |
| 5,421,832 A | 6/1995 | Lefebvre |
| 5,425,744 A | 6/1995 | Fagan et al. |
| 5,427,119 A | 6/1995 | Swartz et al. |
| 5,433,727 A | 7/1995 | Sideris |
| 5,443,454 A | 8/1995 | Tanabe et al. |
| 5,443,478 A | 8/1995 | Purdy |
| 5,451,235 A | 9/1995 | Lock et al. |
| 5,454,365 A | 10/1995 | Bonutti |
| 5,464,408 A | 11/1995 | Duc |
| 5,469,867 A | 11/1995 | Schmitt |
| 5,490,856 A | 2/1996 | Person et al. |
| 5,497,774 A | 3/1996 | Swartz et al. |
| 5,499,975 A | 3/1996 | Cope et al. |
| 5,522,790 A | 6/1996 | Moll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,558,093 A | 9/1996 | Pomeranz |
| 5,558,652 A | 9/1996 | Henke |
| 5,569,204 A | 10/1996 | Cramer |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,662,671 A | 9/1997 | Barbut et al. |
| 5,669,933 A | 9/1997 | Simon et al. |
| 5,693,067 A | 12/1997 | Purdy |
| 5,695,525 A | 12/1997 | Mulhause et al. |
| 5,700,285 A | 12/1997 | Myers et al. |
| 5,702,421 A | 12/1997 | Schneidt |
| 5,704,910 A | 1/1998 | Humes |
| 5,709,224 A | 1/1998 | Behl et al. |
| 5,709,704 A | 1/1998 | Nott et al. |
| 5,709,707 A | 1/1998 | Lock et al. |
| 5,722,400 A | 3/1998 | Ockuly et al. |
| 5,724,975 A | 3/1998 | Negus et al. |
| 5,725,512 A | 3/1998 | Swartz et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,880 A | 5/1998 | Banas et al. |
| 5,749,883 A | 5/1998 | Halpern |
| 5,749,894 A | 5/1998 | Engelson |
| 5,766,219 A | 6/1998 | Horton |
| 5,769,816 A | 6/1998 | Barbut et al. |
| 5,776,097 A | 7/1998 | Massoud |
| 5,782,860 A | 7/1998 | Epstein et al. |
| 5,785,679 A | 7/1998 | Abolfathi et al. |
| 5,800,454 A | 9/1998 | Jacobsen et al. |
| 5,800,457 A | 9/1998 | Gelbfish |
| 5,800,512 A | 9/1998 | Lentz et al. |
| 5,807,261 A | 9/1998 | Benaron et al. |
| 5,810,874 A | 9/1998 | Lefebvre |
| 5,814,028 A | 9/1998 | Swartz et al. |
| 5,814,029 A | 9/1998 | Hassett |
| 5,820,591 A | 10/1998 | Thompson et al. |
| 5,823,198 A | 10/1998 | Jones et al. |
| 5,830,228 A | 11/1998 | Knapp et al. |
| 5,833,673 A | 11/1998 | Ockuly et al. |
| 5,836,913 A | 11/1998 | Orth et al. |
| 5,836,968 A | 11/1998 | Simon et al. |
| 5,840,027 A | 11/1998 | Swartz et al. |
| 5,843,118 A | 12/1998 | Sepetka et al. |
| 5,846,260 A | 12/1998 | Maahs |
| 5,846,261 A | 12/1998 | Kotula et al. |
| 5,848,969 A | 12/1998 | Panescu et al. |
| 5,849,005 A | 12/1998 | Garrison et al. |
| 5,851,232 A | 12/1998 | Lois |
| 5,853,422 A | 12/1998 | Huebsch et al. |
| 5,855,597 A | 1/1999 | Jayaraman |
| 5,865,791 A | 2/1999 | Whayne et al. |
| 5,865,802 A | 2/1999 | Yoon et al. |
| 5,868,708 A | 2/1999 | Hart et al. |
| 5,876,367 A | 3/1999 | Kaganov et al. |
| 5,879,296 A | 3/1999 | Ockuly et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,904,680 A | 5/1999 | Kordis et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Mujis Van de Moer et al. |
| 5,925,074 A | 7/1999 | Gingras et al. |
| 5,925,075 A | 7/1999 | Myers et al. |
| 5,928,192 A | 7/1999 | Maahs |
| 5,928,260 A | 7/1999 | Chin et al. |
| 5,935,145 A | 8/1999 | Villar et al. |
| 5,935,147 A | 8/1999 | Kensey et al. |
| 5,935,148 A | 8/1999 | Villar et al. |
| 5,941,249 A | 8/1999 | Maynard |
| 5,941,896 A | 8/1999 | Kerr |
| 5,947,997 A | 9/1999 | Pavcnik et al. |
| 5,951,589 A | 9/1999 | Epstein et al. |
| 5,951,599 A | 9/1999 | McCrory |
| 5,954,694 A | 9/1999 | Sunseri |
| 5,957,940 A | 9/1999 | Tanner et al. |
| 5,961,545 A | 10/1999 | Lentz et al. |
| 5,976,174 A | 11/1999 | Ruiz |
| 5,980,555 A | 11/1999 | Barbut et al. |
| 5,989,281 A | 11/1999 | Barbut et al. |
| 5,993,469 A | 11/1999 | McKenzie et al. |
| 5,993,483 A | 11/1999 | Gianotti |
| 5,997,557 A | 12/1999 | Barbut et al. |
| 6,004,280 A | 12/1999 | Buck et al. |

| | | | | | | |
|---|---|---|---|---|---|---|
| 6,004,348 | A | 12/1999 | Banas et al. | 6,558,405 B1 | 5/2003 | McInnes |
| 6,007,523 | A | 12/1999 | Mangosong | 6,562,058 B2 | 5/2003 | Seguin et al. |
| 6,007,557 | A | 12/1999 | Ambrisco et al. | 6,589,251 B2 | 7/2003 | Yee et al. |
| 6,010,517 | A | 1/2000 | Baccaro | 6,599,308 B2 | 7/2003 | Amplatz |
| 6,010,522 | A | 1/2000 | Barbut et al. | 6,652,555 B1 | 11/2003 | Van Tassel et al. |
| 6,013,093 | A | 1/2000 | Nott et al. | 6,652,556 B1 | 11/2003 | Van Tassel et al. |
| 6,024,754 | A | 2/2000 | Engelson | 6,666,861 B1 | 12/2003 | Grabek |
| 6,024,755 | A | 2/2000 | Addis | 6,689,150 B1 | 2/2004 | Van Tassel et al. |
| 6,024,756 | A | 2/2000 | Huebsch et al. | 6,702,825 B2 | 3/2004 | Frazier et al. |
| 6,027,520 | A | 2/2000 | Tsugita et al. | 6,730,108 B2 | 5/2004 | Van Tassel et al. |
| 6,033,420 | A | 3/2000 | Hahnen | 6,837,901 B2 | 1/2005 | Rabkin et al. |
| 6,036,720 | A | 3/2000 | Abrams et al. | 6,855,153 B2 | 2/2005 | Saadat |
| 6,042,598 | A | 3/2000 | Tsugita et al. | 6,949,113 B2 | 9/2005 | Van Tassel et al. |
| 6,048,331 | A | 4/2000 | Tsugita et al. | 6,994,092 B2 | 2/2006 | van der Burg et al. |
| 6,051,014 | A | 4/2000 | Jang | 7,011,671 B2 | 3/2006 | Welch |
| 6,051,015 | A | 4/2000 | Maahs | 7,044,134 B2 | 5/2006 | Khairkhahan et al. |
| 6,056,720 | A | 5/2000 | Morse | 7,128,073 B1 | 10/2006 | van der Burg et al. |
| 6,063,070 | A | 5/2000 | Eder | 2001/0020181 A1 | 9/2001 | Layne |
| 6,066,126 | A | 5/2000 | Li et al. | 2001/0034537 A1 | 10/2001 | Shaw et al. |
| 6,068,621 | A | 5/2000 | Balcetta et al. | 2001/0037141 A1 | 11/2001 | Yee et al. |
| 6,074,357 | A | 6/2000 | Kaganov et al. | 2002/0022860 A1 | 2/2002 | Borillo et al. |
| 6,076,012 | A | 6/2000 | Swanson et al. | 2002/0035374 A1 | 3/2002 | Borillo et al. |
| 6,079,414 | A | 6/2000 | Roth | 2002/0045931 A1 | 4/2002 | Sogard et al. |
| 6,080,182 | A | 6/2000 | Shaw et al. | 2002/0062133 A1 | 5/2002 | Gilson et al. |
| 6,080,183 | A | 6/2000 | Tsugita et al. | 2002/0082675 A1 | 6/2002 | Myers |
| 6,083,239 | A | 7/2000 | Addis | 2002/0099439 A1 | 7/2002 | Schwartz et al. |
| 6,090,084 | A | 7/2000 | Hassett et al. | 2002/0138094 A1 | 9/2002 | Borillo et al. |
| 6,096,053 | A | 8/2000 | Bates | 2002/0138097 A1 | 9/2002 | Ostrovsky et al. |
| 6,110,243 | A | 8/2000 | Wnenchak et al. | 2002/0169475 A1 | 11/2002 | Gainor et al. |
| 6,124,523 | A | 9/2000 | Banas et al. | 2002/0177855 A1 | 11/2002 | Greene, Jr. et al. |
| 6,132,438 | A | 10/2000 | Fleischman et al. | 2002/0178570 A1 | 12/2002 | Sogard et al. |
| 6,135,991 | A | 10/2000 | Muni et al. | 2003/0017775 A1 | 1/2003 | Sowinski et al. |
| 6,136,016 | A | 10/2000 | Barbut et al. | 2003/0023266 A1 | 1/2003 | Borillo et al. |
| 6,139,527 | A | 10/2000 | Laufer et al. | 2003/0057156 A1 | 3/2003 | Peterson et al. |
| 6,139,573 | A | 10/2000 | Sogard et al. | 2003/0060871 A1 | 3/2003 | Hill et al. |
| 6,152,144 | A | 11/2000 | Lesh et al. | 2003/0181942 A1 | 9/2003 | Sutton et al. |
| 6,156,055 | A | 12/2000 | Ravenscroft | 2003/0191526 A1 | 10/2003 | Van Tassel et al. |
| 6,161,543 | A | 12/2000 | Cox et al. | 2003/0195555 A1 | 10/2003 | Khairkhahan et al. |
| 6,171,329 | B1 | 1/2001 | Shaw et al. | 2003/0199923 A1 | 10/2003 | Khairkhahan et al. |
| 6,179,859 | B1 | 1/2001 | Bates et al. | 2003/0204203 A1 | 10/2003 | Khairkhahan et al. |
| 6,203,531 | B1 | 3/2001 | Ockuly et al. | 2003/0212432 A1 | 11/2003 | Khairkhahan et al. |
| 6,214,029 | B1 | 4/2001 | Thill et al. | 2003/0220667 A1 | 11/2003 | van der Burg et al. |
| 6,231,561 | B1 | 5/2001 | Frazier et al. | 2004/0034366 A1 | 2/2004 | van der Burg et al. |
| 6,231,589 | B1 | 5/2001 | Wessman et al. | 2004/0044361 A1 * | 3/2004 | Frazier et al. ............ 606/200 |
| 6,245,012 | B1 | 6/2001 | Kleshinski | 2004/0049210 A1 | 3/2004 | Van Tassel et al. |
| 6,251,122 | B1 | 6/2001 | Tsukernik | 2004/0098031 A1 | 5/2004 | van der Burg et al. |
| 6,258,115 | B1 | 7/2001 | Dubrul | 2004/0122467 A1 | 6/2004 | Van Tassel et al. |
| 6,270,530 | B1 | 8/2001 | Eldridge et al. | 2004/0220610 A1 | 11/2004 | Kreidler et al. |
| 6,270,902 | B1 | 8/2001 | Tedeschi et al. | 2004/0230222 A1 | 11/2004 | van der Burg et al. |
| 6,277,138 | B1 | 8/2001 | Levinson et al. | 2005/0004652 A1 | 1/2005 | van der Burg et al. |
| 6,285,898 | B1 | 9/2001 | Ben-Haim | 2005/0113861 A1 | 5/2005 | Corcoran et al. |
| 6,290,674 | B1 * | 9/2001 | Roue et al. ............ 604/107 | 2005/0203568 A1 | 9/2005 | van der Burg et al. |
| 6,290,708 | B1 | 9/2001 | Kugel et al. | | | |
| 6,312,407 | B1 | 11/2001 | Zadno-Azizi et al. | | | |
| 6,328,727 | B1 | 12/2001 | Frazier et al. | | | |

FOREIGN PATENT DOCUMENTS

| | | |
|---|---|---|
| WO | WO 95/04132 | 2/1995 |
| WO | WO 95/22359 | 8/1995 |
| WO | WO 96/01591 | 1/1996 |
| WO | WO 96/40356 | 12/1996 |
| WO | WO 97/28749 | 8/1997 |
| WO | WO 97/35522 | 10/1997 |
| WO | WO 98/02100 | 1/1998 |
| WO | WO 98/17187 | 4/1998 |
| WO | WO 98/23322 | 6/1998 |
| WO | WO 98/27868 | 7/1998 |
| WO | WO 99/05977 | 2/1999 |
| WO | WO 99/07289 | 2/1999 |
| WO | WO 99/08607 | 2/1999 |
| WO | WO 99/23976 | 5/1999 |
| WO | WO 99/25252 | 5/1999 |
| WO | WO 99/30640 | 6/1999 |
| WO | WO 99/44510 | 10/1999 |
| WO | WO 00/16705 | 3/2000 |
| WO | WO 00/27292 | 5/2000 |
| WO | WO 00/67669 | 11/2000 |
| WO | WO 01/08743 A1 | 2/2001 |
| WO | WO 01/15629 A1 | 3/2001 |
| WO | WO 01/30266 A1 | 5/2001 |
| WO | WO 01/30267 A1 | 5/2001 |
| WO | WO 01/30268 A1 | 5/2001 |

Additional US references (continued):

| | | | |
|---|---|---|---|
| 6,342,062 B1 | 1/2002 | Suon et al. | |
| 6,346,116 B1 | 2/2002 | Brooks et al. | |
| 6,361,545 B1 | 3/2002 | Macoviak et al. | |
| 6,364,895 B1 | 4/2002 | Greenhalgh | |
| 6,368,338 B1 | 4/2002 | Konya et al. | |
| 6,371,971 B1 | 4/2002 | Tsugita et al. | |
| 6,375,670 B1 | 4/2002 | Greenhalgh | |
| 6,391,044 B1 | 5/2002 | Yadav et al. | |
| 6,398,803 B1 | 6/2002 | Layne et al. | |
| 6,402,746 B1 | 6/2002 | Whayne et al. | |
| 6,402,779 B1 | 6/2002 | Colone et al. | |
| 6,419,669 B1 | 7/2002 | Frazier et al. | |
| 6,440,152 B1 | 8/2002 | Gainor et al. | |
| 6,443,972 B1 | 9/2002 | Bosma et al. | |
| 6,447,530 B1 | 9/2002 | Ostrovsky et al. | |
| 6,468,291 B2 | 10/2002 | Bates et al. | |
| 6,468,301 B1 | 10/2002 | Amplatz et al. | |
| 6,488,689 B1 | 12/2002 | Kaplan et al. | |
| 6,511,496 B1 | 1/2003 | Huter et al. | |
| 6,514,280 B1 | 2/2003 | Gilson | |
| 6,517,573 B1 | 2/2003 | Pollock et al. | |
| 6,551,303 B1 | 4/2003 | Van Tassel et al. | |
| 6,551,344 B2 | 4/2003 | Thill | |
| 6,558,401 B1 | 5/2003 | Azizi | |

| | | |
|---|---|---|
| WO | WO 02/15793 A2 | 2/2002 |
| WO | WO 02/17809 | 3/2002 |
| WO | WO 02/24106 A2 | 3/2002 |
| WO | WO 02/071977 A2 | 9/2002 |
| WO | WO 03/007825 A1 | 1/2003 |
| WO | WO 03/008030 A2 | 1/2003 |
| WO | WO 03/032818 | 4/2003 |

* cited by examiner

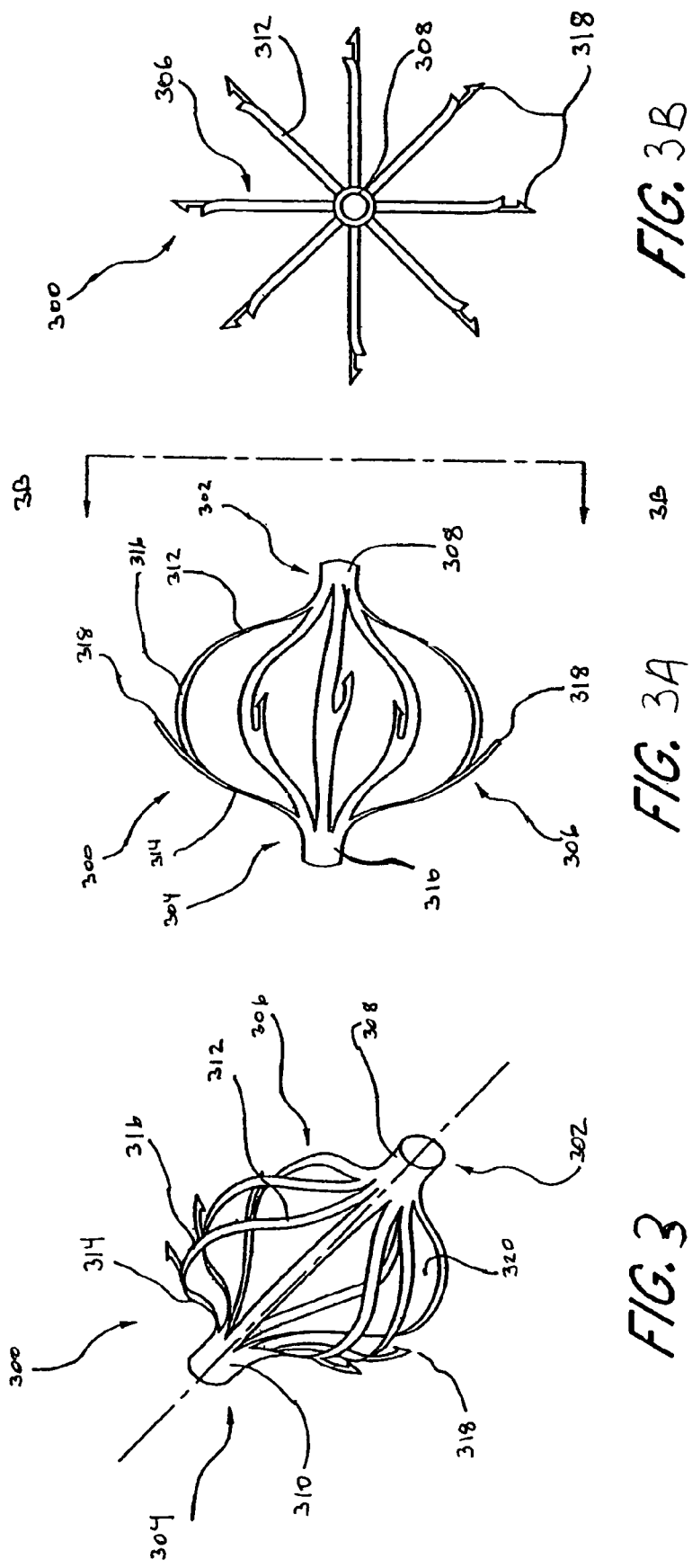

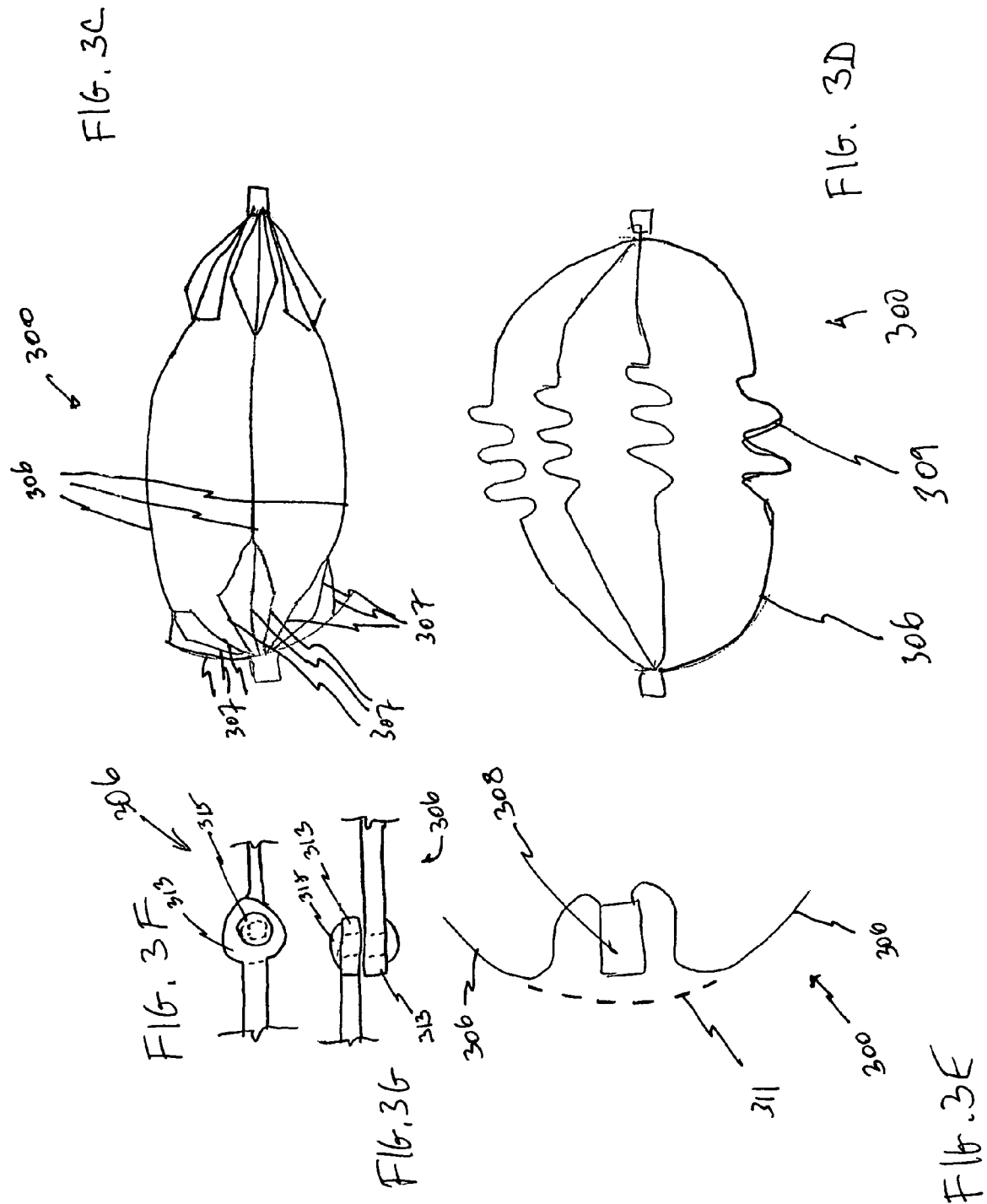

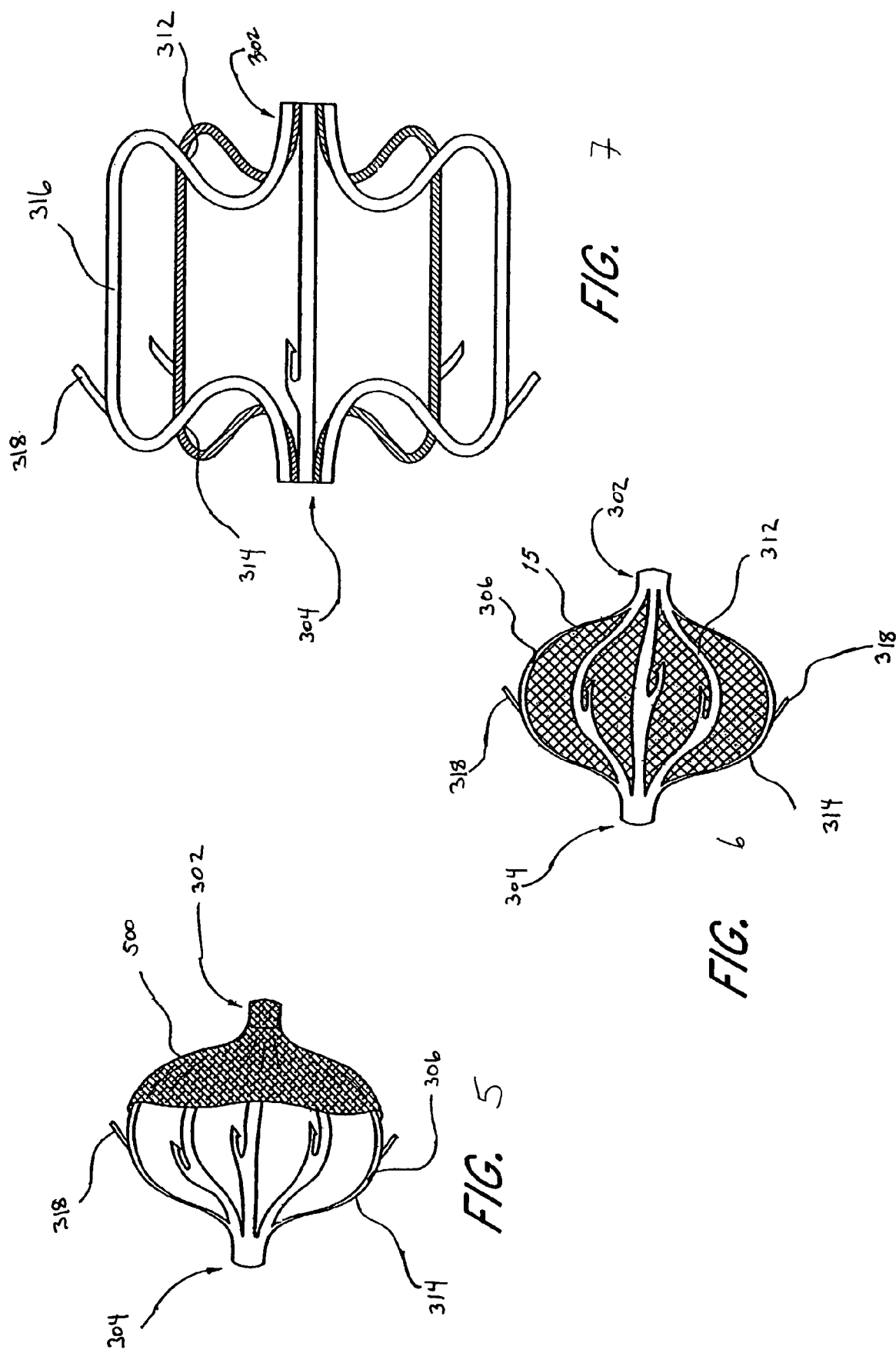

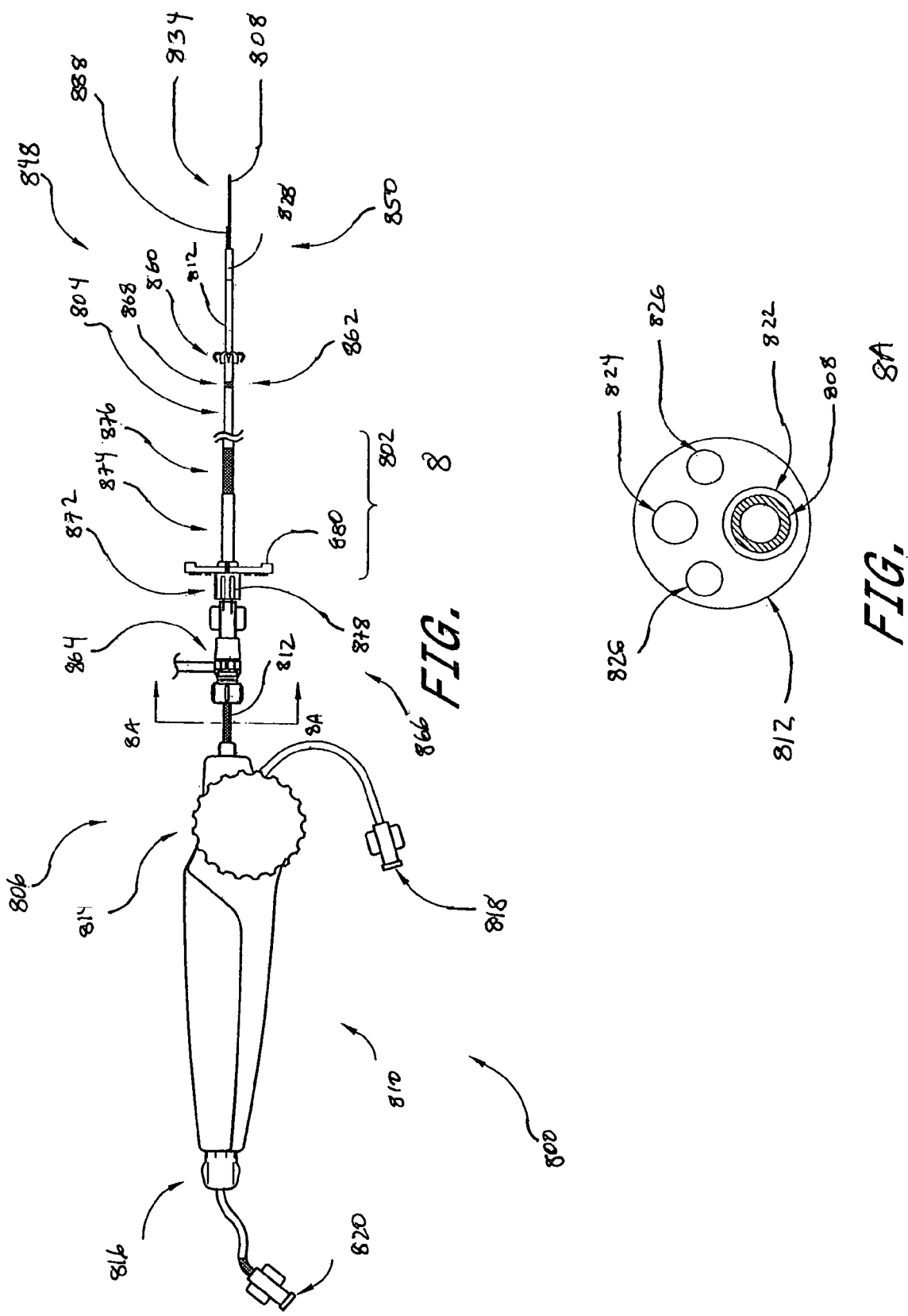

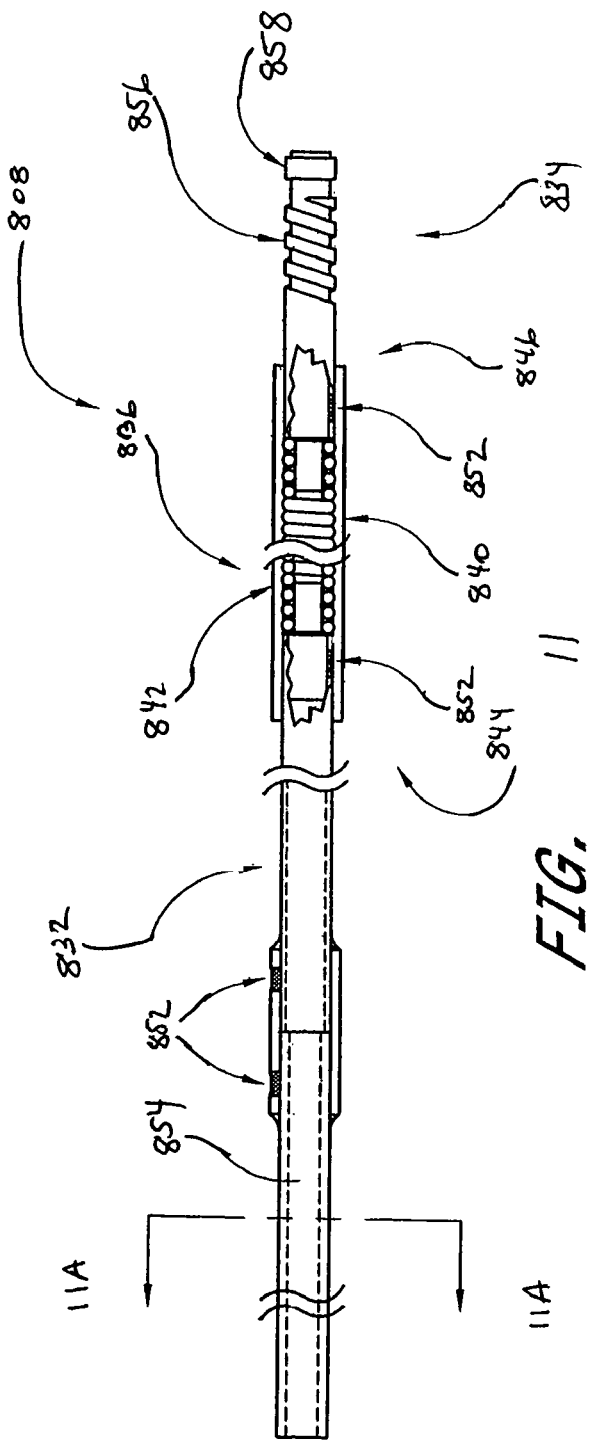
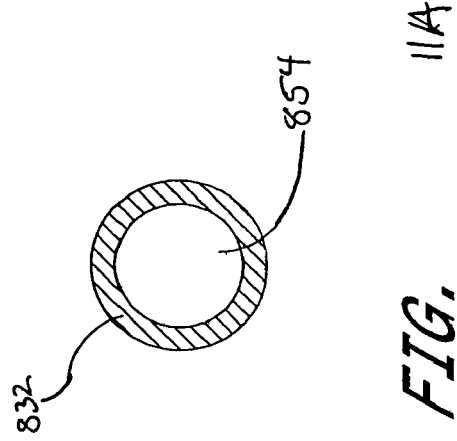
FIG. 11
FIG. 11A

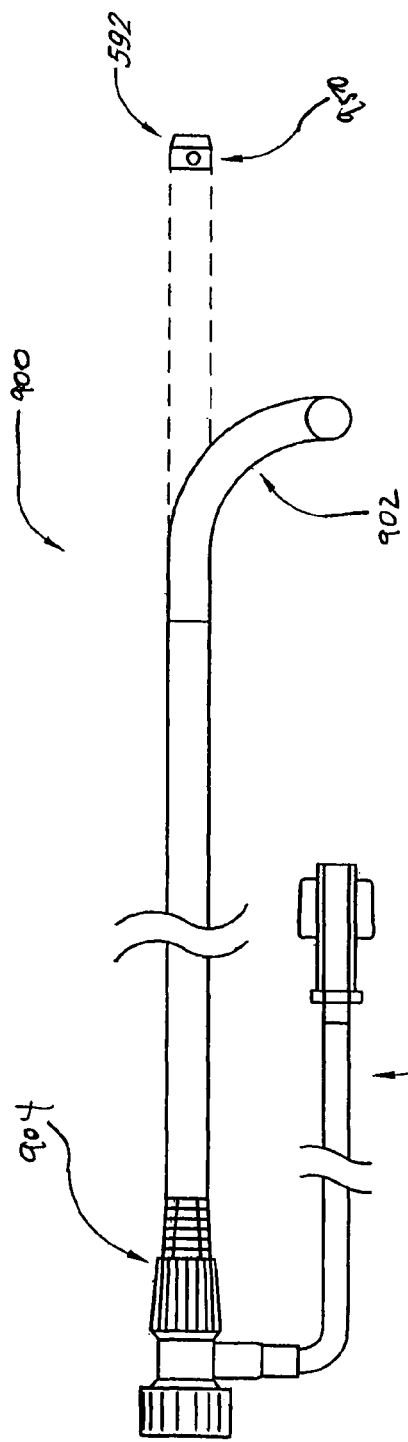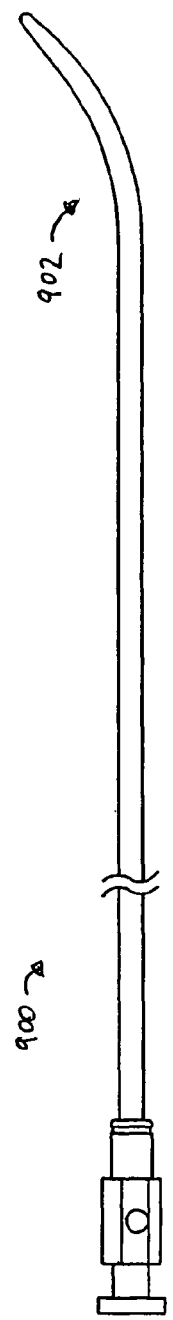
FIG. 13A
FIG. 13B
FIG. 13C

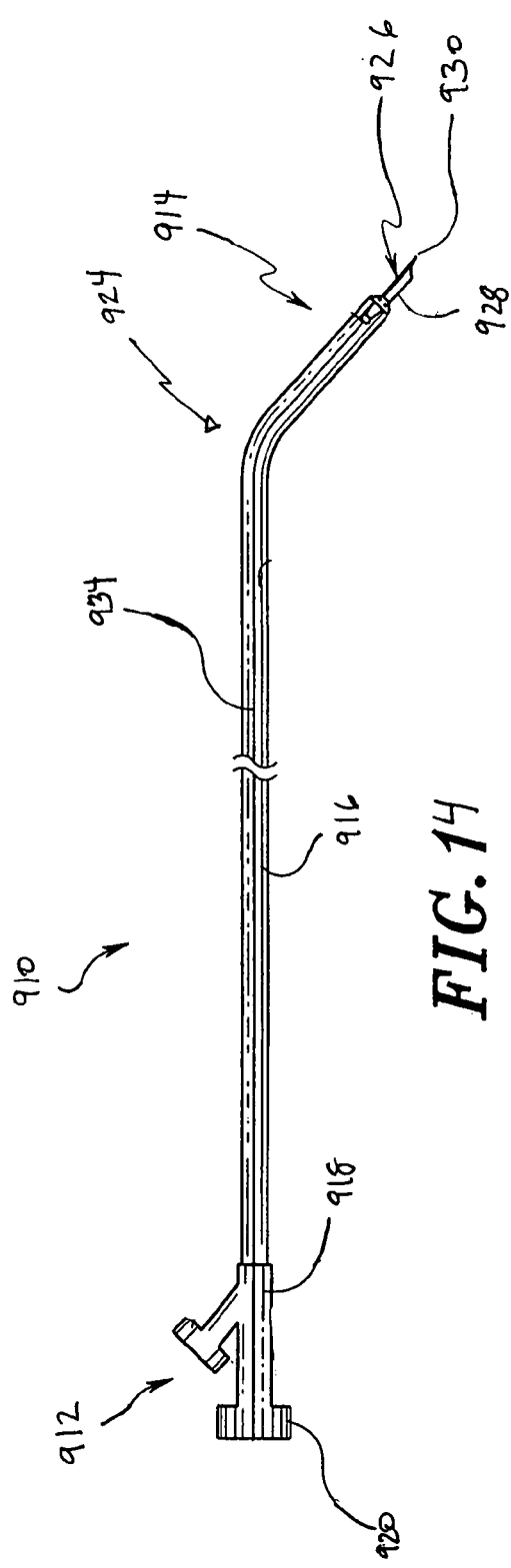
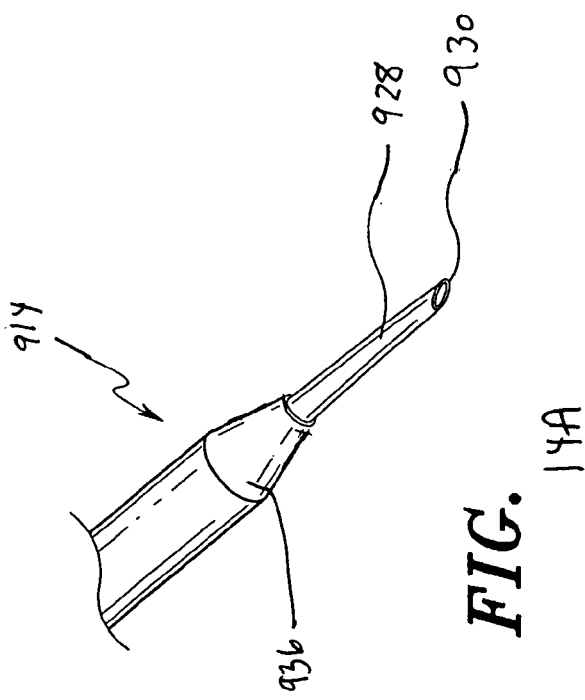
FIG. 14
FIG. 14A

INTRACARDIAC CAGE AND METHOD OF DELIVERING SAME

BACKGROUND

1. Field of the Invention

The present invention relates to methods and devices for closing an opening inside of a body, and in some embodiments, to closing, blocking or filtering the ostium of a left atrial appendage, or a septal defect, such as a patent foramen ovale.

2. Description of the Related Art

Embolic stroke is the nation's third leading killer for adults, and is a major cause of disability. There are over 700,000 strokes per year in the United States alone. Approximately 100,000 of these are hemorrhagic and 600,000 are ischemic (either due to vessel narrowing or to embolism). A large number of strokes are believed to be caused or related to a defect in the heart called a patent foramen ovale, or to thrombus formation due to an irregularity in the heart beat called atrial fibrillation. Although there are pharmacological therapies for stroke prevention such as oral or systemic administration of warfarin or the like, these have been found inadequate due to serious side effects of the medications and lack of patient compliance in taking the medication.

Patent Foramen Ovale

About 50,000 of the ischemic strokes are believed to be caused by a patent foramen ovale. In addition, the risk of recurrent stroke is higher in patients whose strokes are caused by a patent foramen ovale.

The heart is generally divided into four chambers: the upper two are the left and right atria and the lower two are the left and right ventricles. The atria are separated from each other by a muscular wall, the interatrial septum, and the ventricles by the interventricular septum.

Either congenitally or by acquisition, abnormal openings, holes or shunts can occur between the chambers of the heart or the great vessels (interatrial and interventricular septal defects or patent ductus arteriosus and aortico-pulmonary window respectively), causing shunting of blood through the opening. During fetal life, most of the circulating blood is shunted away from the lungs to the peripheral tissues through specialized vessels and foramens that are open ("patent"). In most people these specialized structures quickly close after birth, but sometimes they fail to close. A patent foramen ovale is a condition wherein an abnormal opening is present in the septal wall between the two atria of the heart. An atrial septal defect is a condition wherein a hole is present in the septal wall between the two atria of the heart.

In contrast to other septal defects which tend to have an opening with a generally longitudinal axis approximately normal to the septum, a patent foramen ovale tends to behave like a flap valve. Accordingly, the axis of the patent foramen ovale tends to be at an angle, and almost parallel to the septal wall. The patent foramen ovale is a virtual tunnel, long and wide, but not very tall. It is normally closed because the roof and floor of the tunnel are in contact, but it can open when the pressure in the right side of the heart becomes elevated relative to the pressure in the left side of the heart, such as while coughing.

Studies have shown that adults with strokes of unknown origin (cryptogenic strokes) have about twice the rate of patent foramen ovales than the normal population. Although there is a correlation between strokes and patent foramen ovales, it is currently unknown why this correlation exists. Many people theorize that blood clots and plaque that have formed in the peripheral venous circulation (in the legs for example) break off and travel to the heart. Normally, the clots and plaque get delivered to the lungs where they are trapped and usually cause no harm to the patient. Patients with a patent foramen ovale, however, have a potential opening through which the clots or plaque can pass from the venous circulation and into the arterial circulation. The clots or plaque can then travel to the brain or other tissues to cause a thromboembolic event like a stroke. The clots may pass to the arterial side when there is an increase in the pressure in the right atrium. Then the clots travel through the left side of the heart, to the aorta, and then to the brain via the carotid arteries where they cause a stroke.

Recent studies also suggest a higher incidence of patent foramen ovale in patients suffering from migraine headache, and particularly those who experience aura in association with their migraines, than in the general population. It is theorized that closure of PFO will substantially improve or even cure migraine in these patients, and trials underway suggest that for some patients their migraine was resolved subsequent to closure of their PFO. It has been suggested that migraine could be related to passage through a PFO of gas microemboli, thrombi, or vasoactive chemicals, whereas normally these substances pass through the lungs where they are filtered out or otherwise deactivated.

Previously, patent foramen ovale have required relatively extensive surgical techniques for correction. To date the most common method of closing intracardiac shunts, such as a patent foramen ovale, entails the relatively drastic technique of open-heart surgery, requiring opening the chest or sternum and diverting the blood from the heart with the use of a cardiopulmonary bypass. The heart is then opened, the defect is sewn shut by direct suturing with or without a patch of synthetic material (usually of Dacron, Teflon, silk, nylon or pericardium), and then the heart is closed. The patient is then taken off the cardiopulmonary bypass machine, and then the chest is closed.

In place of direct suturing, closure of a patent foramen ovale by means of a mechanical prosthesis has also been disclosed. A number of devices designed for closure of interatrial septal defects have been used to correct patent foramen ovale. Although these devices have been known to effectively close other septal defects, there are few occlusion devices developed specifically for closing patent foramen ovale.

Atrial Fibrillation

The most common cause of embolic stroke emanating from the heart is thrombus formation due to atrial fibrillation. Approximately 80,000 strokes per year are attributable to atrial fibrillation. Atrial fibrillation is an arrhythmia of the heart that results in a rapid and chaotic heartbeat that produces lower cardiac output and irregular and turbulent blood flow in the vascular system. There are over five million people worldwide with atrial fibrillation, with about four hundred thousand new cases reported each year. Atrial fibrillation is associated with a 500 percent greater risk of stroke due to the condition. A patient with atrial fibrillation typically has a significantly decreased quality of life due, in part, to the fear of a stroke, and the pharmaceutical regimen necessary to reduce that risk.

For patients who develop atrial thrombus from atrial fibrillation, the clot normally occurs in the left atrial appendage (LAA) of the heart. The LAA is a cavity which looks like a small finger or windsock and which is connected to the lateral wall of the left atrium between the mitral valve and the root of the left pulmonary vein. The LAA normally contracts with the rest of the left atrium during a normal heart cycle, thus keeping blood from becoming stagnant therein, but often fails to contract with any vigor in patients experiencing atrial fibrillation due to the discoordinate electrical signals associated with AF. As a result, thrombus formation is predisposed to form in the stagnant blood within the LAA.

Blackshear and Odell have reported that of the 1288 patients with non-rheumatic atrial fibrillation involved in their study, 221 (17%) had thrombus detected in the left atrium of the heart. Blackshear J L & Odell J A., Appendage Obliteration to Reduce Stroke in Cardiac Surgical Patients With Atrial Fibrillation, Ann. Thorac. Surg., 1996.61(2):755-59. Of the patients with atrial thrombus, 201 (91%) had the atrial thrombus located within the left atrial appendage. The foregoing suggests that the elimination or containment of thrombus formed within the LAA of patients with atrial fibrillation would significantly reduce the incidence of stroke in those patients.

As discussed above, pharmacological therapies for stroke prevention such as oral or systemic administration of warfarin or the like have been inadequate due to serious side effects of the medications and lack of patient compliance in taking the medication. Invasive surgical or thorascopic techniques have been used to obliterate the LAA, however, many patients are not suitable candidates for such surgical procedures due to a compromised condition or having previously undergone cardiac surgery. In addition, the perceived risks of even a thorascopic surgical procedure often outweigh the potential benefits. See Blackshear & Odell; see also Lindsay B D, Obliteration of the Left Atrial Appendage: A Concept Worth Testing, Ann. Thorac. Surg., 1996.61(2):515.

Despite the various efforts in the prior art, there remains a need for a minimally invasive method and associated devices for reducing the risk of thrombus formation in the left atrial appendage.

SUMMARY

In one embodiment, a method of preventing ingress of material into the left atrium of a heart includes: providing a delivery sheath having a sheath proximal end, a sheath distal end, and a lumen extending therethrough, to the right atrium of the heart; advancing the sheath distal end through an opening between the right atrium and the left atrium; providing an expandable cage, having a proximal end, a distal end, a plurality of supports extending therebetween, a first membrane provided at the proximal end, and a second membrane provided at the distal end, the expandable cage having a collapsed configuration to be received within the lumen of the delivery sheath, and an expanded configuration for deployment within the heart; delivering the expandable cage to the left atrium of the heart through the delivery sheath; and expanding the expandable cage within the left atrium, the expandable cage when expanded positioning the second membrane at the ostium of the left atrial appendage, wherein the second membrane prevents passage of embolic material from the left atrial appendage into the left atrium, and positioning the first membrane at an opening between the left atrium and a right atrium of the heart, where the first membrane substantially prevents passage of blood between the atria.

The opening can be a natural opening, and the opening can be formed by piercing the atrial septum. In one embodiment, the opening is a patent foramen ovale or a septal defect.

The cage can be self expanding, and can be expanded by retracting the delivery sheath proximally. In one embodiment, the delivering step includes pulling the delivery sheath proximally with respect to the expandable cage prior to said expanding step. In another embodiment, the delivering step includes pushing the expandable cage past the sheath distal end prior to said expanding step. In another embodiment, delivering the expandable cage includes positioning the cage distal of the distal end prior to said expanding step.

The method can further include verifying the position of the expandable cage within the left atrium, wherein said verifying is performed prior to said expanding step, repositioning said cage within the left atrium, and/or retrieving said cage from the left atrium.

In another embodiment of the present invention a method of preventing ingress of material to a chamber of a heart includes: providing an expandable cage to a chamber of a heart, wherein said chamber has at least two openings, and wherein said expandable cage comprises a proximal end, a distal end, a plurality of supports extending therebetween, and at least one membrane, the expandable cage having a collapsed configuration for delivery to the heart, and an expanded configuration for deployment within the heart; and expanding said expandable cage within the chamber of the heart, wherein said at least one membrane is positioned at one of said at least two openings of the chamber to prevent ingress of material into the chamber.

One of said at least two openings can be an ostium to a left atrial appendage, a patent foramen ovale, or a septal defect. The membrane can filter blood from a left atrial appendage and/or substantially prevent blood flow from a right atrium into a left atrium the heart.

In another embodiment, an expandable cage for preventing ingress of material to a chamber of a heart includes: a frame including a proximal end, a distal end, and a plurality of supports extending therebetween, wherein said cage has a collapsed configuration for delivery to a chamber of the heart, and an expanded configuration for deployment within the heart; and at least one membrane provided at least one of said proximal and said distal ends, wherein a length between said proximal and distal ends when at least partially expanded generally approximates the distance between an ostium of a left atrial appendage and a septum of the heart.

The at least one membrane can include a proximal membrane provided at said proximal end and a distal membrane provided at said distal end. The at least one membrane can have a diameter corresponding to the dimensions of a patent foramen ovale or a diameter corresponding to the dimensions of an ostium of a left atrial appendage. In another embodiment, the proximal end includes supports that extend proximally, distally, and proximally from an apex to a proximal hub.

In yet another embodiment of the present invention, a system for preventing ingress of material to a chamber of a heart includes and expandable cage; and a transseptal sheath for delivering the expandable cage to the chamber.

BRIEF DESCRIPTION OF THE DRAWINGS

FIG. 3 is a perspective view of an intracardiac cage in accordance with one embodiment of the present invention;

FIG. 3A is a side elevational view of the intracardiac cage of FIG. 3;

FIG. 3B is an end view taken along the line 3B-3B of FIG. 3A;

FIG. 3C is one embodiment of an intracardiac cage having branched portions;

FIG. 3D is one embodiment of an intracardiac cage having serpentine spring portions;

FIG. 3E is one embodiment of the end portion of an intracardiac cage;

FIG. 3F is a top view of a fracturable support;

FIG. 3G is a side view of the fracturable support of FIG. 3F;

FIGS. 5-7 are perspective views of an intracardiac cage according to additional embodiments of the present invention;

FIGS. 8-9 are perspective views of a delivery system for delivering the intracardiac cage of FIGS. 3-7 to a desired location within the heart;

FIG. 11 is a partial cross-sectional view of the axially moveable core of FIGS. 8-10;

FIG. 11A is a cross-sectional view taken along line 11A-11A of FIG. 11;

FIGS. 13A-13C are perspective views of a transseptal sheath in accordance with embodiments of the present invention;

FIG. 14 is a perspective view of a dilator in accordance with one embodiment of the present invention;

FIG. 14A is a detailed view of the distal end of the dilator of FIG. 14; and

DETAILED DESCRIPTION

Some embodiments of the present invention are described primarily in the context of a left atrial appendage, septal defect or patent foramen ovale closure device or procedure; however, the devices and methods herein are readily applicable to a wider variety of closure or attachment procedures, and all such applications are contemplated by the present inventors. Vascular procedures such as patent ductus arteriosis closure, isolation or repair of aneurysms, or occlusion of vessels, ducts, or conduits, may also be accomplished using the devices as described herein. A variety of other tissue openings, lumens, hollow organs and surgically created passageways may be closed in accordance with the preferred embodiments. Closures and repairs described herein may be accomplished using catheter based interventional methods or minimally invasive surgical methods. Adaptation of the devices and methods disclosed herein to accomplish procedures such as the foregoing will be apparent to those of skill in the art in view of the disclosure herein.

The Heart

Figure 1A:
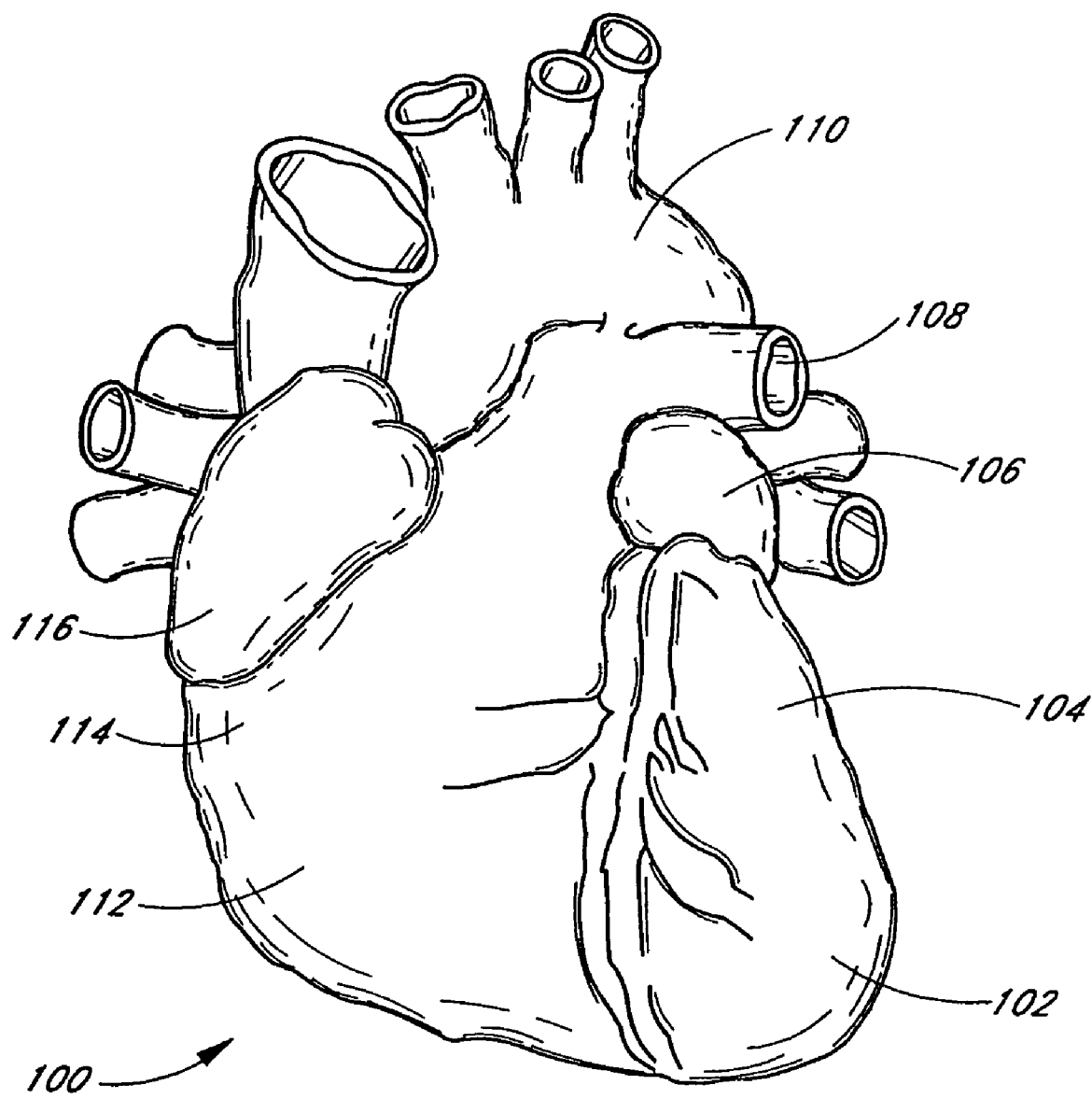
FIG. 1A is an anterior illustration of a heart, with the proximal portions of the great vessels.

FIG. 1A is a heart 100 and certain portions including the left ventricle 102, the left atrium 104, the left atrial appendage 106, the pulmonary artery 108, the aorta 110, the right ventricle 112, the right atrium 114, and the right atrial appendage 116. The left atrium 104 is located above the left ventricle 102 and the two are separated by the mitral valve (not illustrated).

Figure 1B:
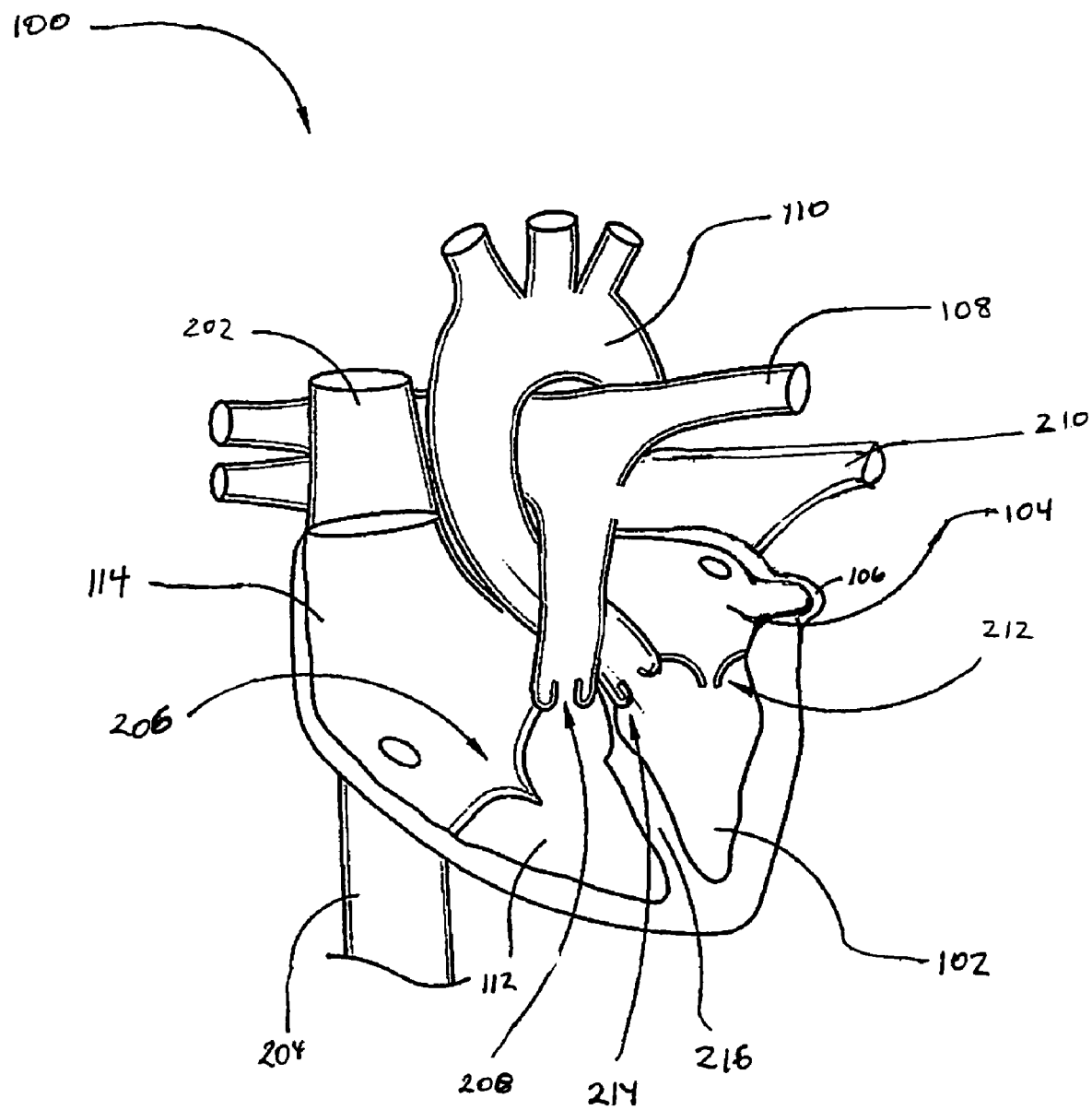
FIG. 1B is a partial cross-sectional view of the heart of FIG. 2.

FIG. 1B is a partial cross-sectional view of the heart 100 of FIG. 1A with additional features shown. Deoxygenated blood generally enters the right atrium 114 from the upper portion of the body via the superior vena cava 202 and from the lower portion of the body via the inferior vena cava 204. The blood is pumped from the right atrium 114 into the right ventricle 112 through the tricuspid valve 206 and then to the lungs (not shown) through the pulmonary valve 208 and pulmonary arteries 108.

Oxygenated blood returns to the heart 100 from the lungs via the pulmonary veins 210, which direct the blood into the left atrium 104. As the heart 100 pumps, the oxygenated blood passes from the left atrium 104 into the left ventricle 102 via the mitral valve 212. Blood exits the left ventricle 102 via the aortic valve 214 and aorta 110, which distributes the oxygenated blood to the body via the circulatory system.

A septum 216 separates the left side of the heart 100 from its right side, and prevents blood from flowing directly therebetween. In particular, an interatrial septum (not shown) separates the right atrium 114 from the left atrium 104, and an interventricular septum separates the right ventricle 112 from the left ventricle 102. The interatrial septum and interventricular septum are sometimes referred to as the atrial septum and ventricular septum, respectively.

In some clinical situations there is a hole or defect in the septum 216 of the heart 100, which allows blood to flow directly from the right atrium 114 to the left atrium 104, or from the right ventricle 112 to the left ventricle 102. It is often clinically desirable to seal or close off such holes or defects. In addition, in patients that suffer from atrial fibrillation, it is often desirable to seal, close off, block, or filter the opening between the left atrium 104 and the left atrial appendage 106 of the heart 100.

Intracardiac Cages

Embodiments of structures suitable for blocking an opening to a chamber of the heart are illustrated in FIGS. 2-7. It should be understood that although the embodiments described herein may be referred to as blocking, the same embodiments are also suitable for filtering, sealing, closing off, or plugging, both totally or partially.

Figure 2:
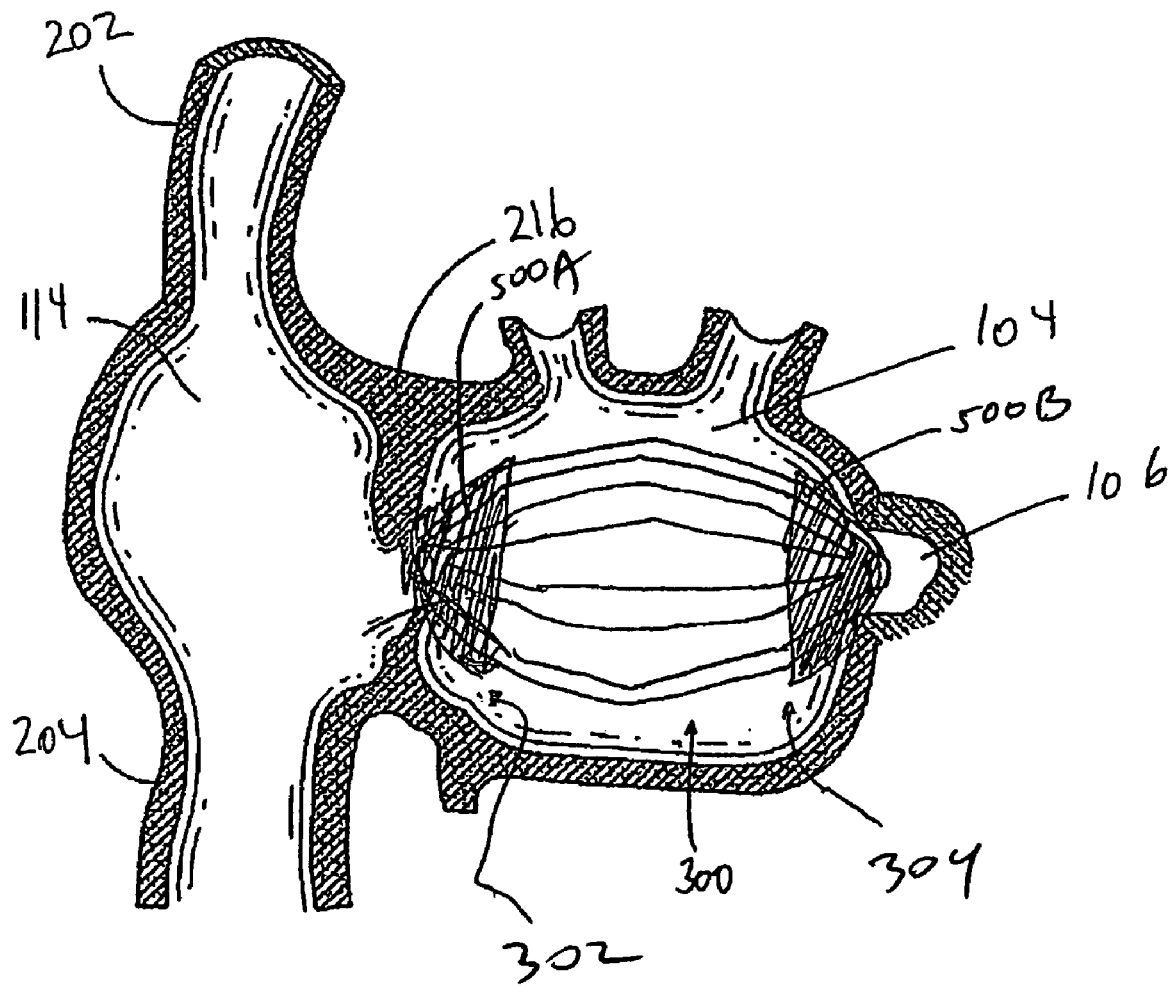
FIG. 2 is a schematic, partial cross-sectional view of an intracardiac cage implanted in a chamber of a heart.

FIG. 2 illustrates one embodiment of an intracardiac cage 300 implanted in a left atrium 104 of a patient. The cage 300 has a proximal end 302 positioned against the atrial septum 216, and a distal end 304 positioned against the ostium of the left atrial appendage 106. A first membrane 500A is provided at the proximal end of the cage 300 to create a barrier to the ingress of material, such as particles or fluid or both, into the left atrium 104 through any opening that may be located in the atrial septum 216, such as a septal defect, patent foramen ovale, or a puncture opening used for accessing the left atrium 104. In addition, the intracardiac cage 300 may be used to close multiple atrial septal defects occurring in a patient's heart. A second membrane 500B is provided at the distal end of the cage 300 to create a barrier to the ingress of material, such as particles or fluid or both, into the left atrium 104 from the left atrial appendage 106.

The cage 300 may have any suitable configuration adapted to span the distance between the septum 216 and the atrial appendage 106 and position the membranes 500A and 500B across an opening in the septum 216 and the ostium of the atrial appendage 106. Although two membranes 500A, 500B are illustrated on the cage 300, it will be appreciated that only one membrane may be used, if desired, to provide a barrier to either a septal opening or the atrial appendage, or more than two membranes may be used to prevent ingress of material from other openings into the chamber. In another embodiment, the cage 300 does not include a membrane. Instead, the cage itself acts as a barrier to substantially prevent ingress of particles, fluids, or both into the left atrium.

The cage 300 is preferably expandable within the left atrium to provide sufficient force to hold the membranes 500A and 500B against the respective openings. In one embodiment, the cage 300 is self-expanding, such that in the configuration shown in FIG. 2, the cage 300 is in a mostly, but not completely, expanded configuration, to hold the cage in place. In other embodiments, the cage 300 may be manually expanded, such as by inflation of a balloon or other mechanism, with the cage 300 locking itself in the desired configuration within the heart.

In one embodiment, any of a variety of active expansion devices are used to expand the cage 300 within a patient. For example, telescoping tubes can be used to expand the cage 300. An inner tube can be positioned in contact with the distal end of a cage 300 and an outer tube can be positioned in contact with the proximal end of the cage 300. By moving the outer tube distally with respect to the inner tube, distal force can be applied to the proximal end of the cage 300, thereby causing the cage 300 to change its shape from reduced-diameter configuration to an expanded-diameter configuration.

The amount of cage 300 expansion can be controlled by any of a variety of mechanisms, such a lock placed on either or both of the telescoping tubes to fix its position when the tubes achieve a predetermined or desired separation. In addition, a ratchet can be used to fix the separation between the telescoping tubes. Telescoping tubes and other embodiments of cage 300 expansion devices are described in U.S. application Ser. No. 10/426,107, filed Jul. 30, 2002, which is incorporated by reference herein. One of skill in the art will appreciate that although the expansion devices and structures described in the aforementioned application are configured for an implantable device for placement within a left atrial appendage, these teachings can readily be applied to a cage as described herein for placement within an atrium. Similarly, the devices and methods described in the other patents and applications incorporated by reference hereinbelow can also be adapted to the expandable cage described herein. The cage 300 in one embodiment has a length between the proximal and distal ends of about 2 cm to about 10 cm, more preferably about 5 cm to about 7 cm, to correspond to the size of the left atrium 104.

An intracardiac cage 300 in accordance with one embodiment of the present invention is illustrated in FIGS. 3-3F, without showing the membranes 500A and 500B. The cage 300 has a proximal end 302, a distal end 304, and a longitudinal axis extending therebetween. A plurality of supports 306 extend between a proximal hub 308 and a distal hub 310. The cage 300 can include at least two or three supports 306, and in some embodiments, includes at least about ten supports 306. In one embodiment, sixteen supports 306 are provided. In another embodiment illustrated in FIG. 3C, the supports 306 are branched into branches 307 to provide mechanical coverage at the ends 302, 304 of the cage 300 and reduce the mechanical coverage in the non-barrier, central, or mid portion of the cage 300. The branches 307 can be provided at proximal end 302, the distal end 304, or both ends 302, 304 of the cage 300.

In another embodiment illustrated in FIG. 3D, the supports 306 include curves 309, such as serpentine curves or s-shaped curves, to provide an overall deployed length that can vary to fit a variety of atrium lengths yet collapse into a delivery catheter. The curves 309 can be positioned at any one or a combination of the proximal end 302, distal end 304, or mid portion of the cage 300. In one embodiment, the tissue-contacting surface of the curves 309 is formed within the outer surface defined by the cage 300. The curves 309 of the cage 300 provide length adjustability during cage 300 deployment. The supports 306 can be deployed substantially in contact with the inner surface of the atrium to reduce blood flow disturbances. Blood flow disturbances can be a cause of thrombus formation and thrombus can embolize, potentially causing infarcts and/or strokes.

The precise number and configuration of supports 306 can be modified depending upon the desired physical properties of the cage 300, as will be apparent to those of skill in the art in view of the disclosure herein without departing from the present invention. The cage 300 can also include an occluding member (not shown) and any of a variety of stabilizing members, such as those described in U.S. application Ser. No. 09/435,562, filed Nov. 8, 1999, and U.S. application Ser. No. 10/033,371, filed Oct. 19, 2001, published as U.S. Publication No. 2002/0111647, which are incorporated by reference. The supports 306 are generally sufficiently spaced apart from one another to allow blood to flow between them.

In another embodiment, the proximal hub 308, distal hub 310, or both, and the associated supports 306 can be shaped as shown in FIG. 3E, in which the hub 308, 310 is at least partially recessed. For example, the hub 308, 310 can be recessed relative to the surface defined by projecting the supports in a continuous curve 311, such as that shown as the dashed line in FIG. 3E. This recessing either or both of the hubs 308, 310 may be employed with any of the embodiments shown herein. The hub 308, 310 can be recessed so that when deployed, it does not cause irritation or tissue damage to the heart.

Each support 306 can include a proximal spoke portion 312, a distal spoke portion 314, and an apex 316. Each of the proximal spoke portion 312, distal spoke portion 314 and apex 316 can be a region on an integral support 306, such as a continuous rib or frame member which extends in a generally curved configuration as illustrated, with a concavity facing towards the longitudinal axis of the cage 300. A distinct point or hinge at apex 316 can or can not be provided.

The cage 300 may be reduced in diameter to a reduced or collapsed configuration for transluminal delivery to the heart, as will be described in greater detail below. Once delivered to the heart, the cage 300 diameter can be expanded to an expanded configuration for placement and securement at the desired location within the heart 100. In one embodiment, the cage 300 may be self-expanding, with supports made of a superelastic material such as nickel titanium alloy or nitinol. To collapse the cage 300, the supports 306 may be extended axially to a generally linear configuration, with the distance between the proximal and distal hubs 308, 310 increasing. In another embodiment, the cage 300 may be collapsed to its reduced configuration while maintaining the distance between the proximal and distal hubs 308, 310 substantially constant, such as by folding the supports 306 upon themselves or otherwise collapsing the supports 306 while holding the relative position of the proximal and distal ends 302, 304. Even more preferably, the supports 306 may not only collapse upon themselves, but the distance between the proximal and distal hubs 308, 310 may decrease when the cage 300 is moved to its collapsed configuration, such as by pulling the distal end 304 toward the proximal end 302, or pushing the proximal end 302 toward the distal end 304, or both. Then, when the cage 300 expands, it expands not only radially outwardly, but also axially to increase the distance between the proximal and distal hubs 308, 310. Such an embodiment may facilitate placement of the cage 300 within a chamber of the heart 100, as described below.

Some of the supports 306, and in some cases each support 306, can be provided with one or two or more anchors or barbs 318 to help secure or anchor the cage 300 at the desired location within the heart 100. In the configuration illustrated in FIG. 3, with the cage 300 in its enlarged orientation, each of the barbs 318 projects generally radially outwardly from the longitudinal axis, and is inclined in the proximal direction. One or more barbs 318 may also be inclined distally, orthogonally, perpendicularly, inwardly, outwardly, and/or to the side, as may be desired by the particular clinical use. In a preferred embodiment enough barbs 318 are provided to prevent the cage from rotating relative to the atrial wall. For example, in one embodiment, at least one barb 318 is directed in each of a proximal, distal, and transverse direction with respect to a support 306 to prevent the cage 300 from rotating relative to the atrial wall. In one embodiment, the cage 300 includes three barbs 318. In another embodiment, the cage 300 includes four barbs. In one embodiment, the barbs 318 and corresponding support 306 are cut from a single ribbon, sheet or tube stock and the barb 318 inclines radially outwardly at approximately a tangent to the curve formed by the support 306. In one embodiment the cage 300 includes no barbs 318 at all.

The term "barb" is a broad term intended to have its ordinary meaning. The term "barb" can include any of a variety of anchors, locks, adhesives, clips, clamps, coils, springs, and/or hooks known to those of skill in the art. The barb can be any device that holds, secures, fixes, locks, and/or maintains the position of an implantable device, such as an intracardiac cage 300, either partially, substantially, or totally, within the heart. In some embodiments, the barbs are projections that do not come to a point, such as a catch and release hook. Barbs may have traumatic or atraumatic tips, or a combination thereof. In addition, the barbs can engage, penetrate, pierce, pinch, press, and/or grasp the tissue at the inside wall of the heart.

In some embodiments, the cage 300 can be deployed or recovered using a delivery system, as described in greater detail below. Cage 300 recovery can be facilitated by the anchor or barb design. For example, the anchors or barbs can pronate such that they do not 'catch' on a delivery catheter during cage recovery or implant delivery. In one embodiment barbs move into the planes of the supports during withdrawal of the cage into a catheter, thereby preventing the barbs from contacting the distal end of the catheter and impeding withdrawal of the cage into the catheter. In another embodiment, the barbs move inward to the planes of the supports during withdrawal of the cage 300 into a catheter. Implantable devices including pronating anchors and barbs are disclosed in U.S. application Ser. No. 10/838,710, filed May 4, 2004, which is incorporated by reference herein.

In some embodiments the barbs allow tissue ingrowth, and in other embodiments they prevent tissue ingrowth. In one embodiment, the support 306 has a center portion that is fractureable, which permits the cage 300 to separate into two portions. Cage fracture may be desirable for hearts which become enlarged, or which contract in overall size, over time. In such embodiments, the barbs preferably promote tissue ingrowth, which allows permanent anchoring of each cage 300 portion within the heart. In one such embodiment, the barbs 318 are located only at the proximal and distal ends 302, 304 of the cage 300, and not in the center portion 313. One embodiment of a fracturable support 306 is illustrated in FIGS. 3F and 3G. In one embodiment, the fracturable support 306 has two atraumatic loop ends 313 that are coupled to one another with a rivet 315. The rivet 315 can be made from a bioresorbable material so that it dissolves over time.

Anchoring of the cage 300 relative to the atrial wall may be desirable to prevent cardiac tissue irritation, erosion, or damage; to prevent irritation or disruption of conduction pathways in the heart tissue, to orient supports in relation to blood flow pathways such as the pulmonary vein or the mitral valve.

The cage 300 illustrated in FIG. 3 may be constructed in any of a variety of ways, as will become apparent to those of skill in the art in view of the disclosure herein. In one method, the cage 300 is constructed by laser cutting a piece of tube stock to provide a plurality of axially extending slots in-between adjacent supports 306. Similarly, each barb 318 can be laser cut from the corresponding support 306 or space in-between adjacent supports 306. Generally axially extending slots 320 separate adjacent supports 306 and end a sufficient distance from each of the proximal end 302 and distal end 304 to create a proximal hub 308 and a distal hub 310 to which each of the supports 306 is attached. In this manner, an integral cage 300 is formed.

Alternatively, each of the components of the cage 300 may be separately formed and attached together such as through soldering, brazing, heat bonding, adhesives, and other fastening techniques which are known in the art. Another method of manufacturing the cage 300 is to laser cut a slot pattern on a flat sheet of appropriate material, such as a flexible metal or polymer. The flat sheet may thereafter be rolled about an axis and opposing edges bonded together to form a tubular structure. In another embodiment, the cage 300 is manufactured by braiding a structure, such as wire filament, into a cylindrical configuration and crimping the braided ends into radiopaque tubes. Such devices and methods are described in U.S. Pat. No. 6,325,815, which is incorporated by reference herein.

The apex portion 316, which can also carry a barb 318 may be advanced from a low profile, compressed, or reduced-diameter orientation (not shown) in which each of the supports 306 extend generally parallel to the longitudinal axis, to an implanted, expanded or enlarged-diameter orientation as illustrated, in which the apex 316 and its barb 318 are positioned radially outwardly from the longitudinal axis. The support 306 may be biased towards the enlarged orientation, or may be advanced to the enlarged orientation under positive force following positioning within a desired tubular anatomical structure, in any of a variety of manners.

Figure 4:
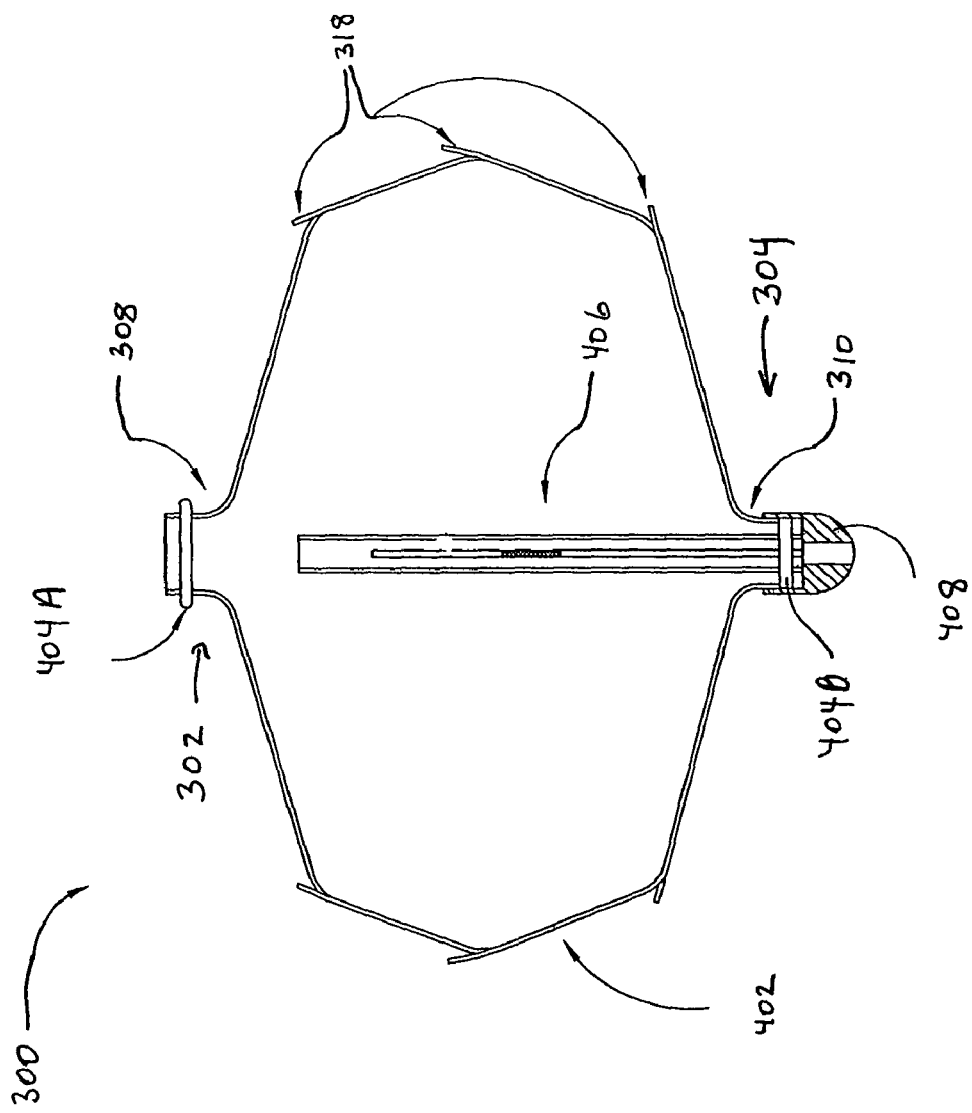
FIG. 4 is a partial cross-sectional view of an intracardiac cage according to another embodiment of the present invention.

A cross-sectional view of another embodiment of an intracardiac cage 300 is shown in FIG. 4. The cage 300 preferably is available in a range of sizes to accommodate the anatomy of a patient's heart 100. The cage 300 preferably includes a frame 402 and a membrane (not shown) on the proximal face or end 302 of the cage 300 and/or distal face or end 304 of the cage 300. The frame 402 can be constructed of self-expanding nitinol supports 306. The membrane preferably is constructed of a fabric covering, such as one made of expanded polytetrafluoroethylene (ePTFE), or an ePTFE/polyethylene (PE) laminate. To attach the membrane to the frame 402, a PE mesh preferably is placed against the supports 306, with one sheet of ePTFE preferably placed over the PE mesh and another sheet of ePTFE preferably placed on an opposite side of the supports 306. The membrane preferably is heated on both sides causing the PE to melt into both sheets of ePTFE, thereby surrounding a portion of the frame 402. The nitinol supports 306 allow the cage to self-expand in the desired portion of the heart 100, and can be expanded such that the membrane covers, blocks, filters, contacts, engages, or applies pressure to a desired anatomical surface, area, region, orifice, ostium, hole or defect. The ePTFE/PE lamination is generally partially porous, and facilitates rapid endothelialization and healing.

The membrane can include implant grade filter or barrier materials such as polyester, polyurethane, polyethylene, expanded polytetrafluoroethylene (ePTFE), polypropylene mesh, metal mesh, including Nitinol, stainless steel, and other metals, and other filter or barrier materials as are commonly known in the art. The membrane can include an impervious film, and in some cases can have openings to enhance fluid flow therethrough. The openings can be created by any of a variety of methods, including laser drilling, piercing, etc. The membrane can be a woven, non-woven, knitted, cast, spun, electrospun, laminated, blow-molded, or otherwise fabricated material.

The membrane can be attached to the supports 306 by heat-fusing, with or without an intermediate adhesive layer, by encircling supports and attaching the membrane to itself using any of a variety of techniques, such as heat fusing, solvent welding, ultrasonic welding, by using adhesives, by mechanical interlock, or by other means as are known in the art.

The membrane can be configured to provide a impervious barrier function to some or all of any substances desired, such as substances thought to be a significant causative factor in stroke or migraine, including but not limited to particles, emboli, thromboemboli, gas bubbles, vasoactive chemicals, neuromediators, or other substances normally filtered by or otherwise deactivated by the lungs. The membrane can be configured to filter some or all of such substances. The membrane can be configured to de-activate or remove from the bloodstream some or all of any substances thought to be a significant causative factor in stroke or migraine, including but not limited to those listed above. One or more membranes may be applied to the supports 306, and each membrane applied may have different barrier, filter, or de-activation characteristics, and any single membrane may have regions with differing barrier, filter, or de-activation characteristics.

As shown in FIG. 4, the cage 300 preferably extends from a proximal end or hub 302 to a distal end or hub 304. In some embodiments, the proximal hub 302 is coupled with a crosspin 404A. In some embodiments the distal hub 304 is coupled with a slider assembly 406, as described in U.S. application Ser. No. 10/642,384, filed Aug. 15, 2003, which is incorporated by reference in its entirety. The distal hub 304 preferably is coupled with an implant plug 408. In one embodiment, the implant plug 408 comprises an atraumatic tip, such that contact between the atraumatic tip and the inside surface of the heart 100 does not cause substantial damage or trauma to the heart 100. The distal hub 304 may also be used to extend into the left atrial appendage to hold the cage in place. A crosspin 404B secures the implant plug 408 to the distal end or hub 304. The cage 100 preferably is expandable and collapsible, as described above, and can include anchors 318 that extend from the frame 402 when the cage 300 is expanded, as described above.

FIGS. 5-7 illustrate additional embodiments of an intracardiac cage 300 in accordance with additional embodiments of the present invention. The cage 300 may be provided with a barrier 500, such as a mesh or fabric as has been previously discussed. The barrier 500 may be provided on only one half or hemisphere, such as proximal face 302 as illustrated, on both faces (not shown), or may be carried by the entire cage 300 from its proximal end 302 to its distal end 304 provided the barrier has suitable flow properties for the chosen configuration. The barrier 500 may be secured to the radially inwardly facing surface of the supports 306, as illustrated in FIG. 6, or may be provided on the radially outwardly facing surfaces of the supports 306, or both.

Another embodiment of an intracardiac cage 300 is illustrated in FIG. 7, in which the apex 316 is elongated in an axial direction to provide additional contact area between the cage and the wall of the anatomical structure into which it is to be inserted. In this embodiment, one or two or three or more anchors or barbs 318 may be provided on each support 306, depending upon the desired clinical performance. The cage 300 illustrated in FIG. 7 may also be provided with any of a variety of other features discussed herein, such as a partial or complete barrier 500. In addition, the cage 300 of FIG. 7 may be enlarged or reduced in diameter using any of the techniques disclosed elsewhere herein.

The intracardiac cage 300 can be any of a variety of shapes, including spherical, elliptical, hexagonal, octagonal, or any other symmetric or asymmetric shape. The cage 300 can have an s-shaped, c-shaped, and/or a u-shaped portion. The cage 300 can act like a spring and spring into its expanded shape when released from the delivery system, as described in greater detail below. The cage supports can be oriented substantially axially relative to a line from hub to hub or can have a spiral orientation relative to this line.

Delivery Systems

The intracardiac cage 300 as described above may be delivered to the left atrium 104 of a patient by any suitable method. In one embodiment, a transseptal sheath, such as described below, may be delivered into the left atrium 104 through the septum 216 from the right atrium 114, with a self-expanding cage 300 collapsed within the transseptal sheath at its distal end. The transseptal sheath may pass through or pierce any suitable portion of the septum 216, including the fossa ovalis, a septal defect, the patent foramen ovale, or any other portion, including a healthy portion, of the septum 216. A distal end of the sheath may be positioned at the ostium of or within the left atrial appendage 106. A push rod may be inserted into the transseptal sheath to engage the proximal end of the cage 300. In one embodiment, the push rod may releasably engage the cage 300, such as with a threaded connection, simple contact, or other mechanism. With the distal end of the transseptal sheath, and correspondingly, the distal end 304 of the cage 300, at the ostium of or within the left atrial appendage 106, the transseptal sheath may be retracted proximally, while maintaining the push rod against the cage 300. As the transseptal sheath is retracted, the cage 300 is exposed and self-expands to engage against the walls of the left atrium 104. In one embodiment, the transseptal sheath is withdrawn until the tip of the sheath is barely (e.g., 1-2 mm) within the left atrium, and thereafter the push rod is advanced to fully deploy the cage. At this point the transseptal sheath is fully withdrawn from the septum until the tip of the sheath is within the right atrium. In one embodiment, the push rod is hollow to allow radiopaque contrast dye injections and associated physician evaluation before, during, and after cage deployment.

In one embodiment, the push rod is hollow, and a core extends through the push rod and releasably engages the distal end 304 of the cage 300. When the cage 300 is collapsed in the transseptal sheath, the distance between the proximal and distal ends 302, 304 of the cage 300 may be reduced relative to its expanded configuration by relative movement of the core and the push rod. Then, when the transseptal sheath is retracted from the cage 300, the core and the push rod may be moved relatively to cause the proximal and distal ends 302, 304 of the cage 300 to move away from each other, relieving stress in the cage 300 and allowing it to expand not only radially but also axially. This causes the cage 300 to expand outwardly against the septum 216 and the ostium of the left atrial appendage 106, providing a holding force to hold the membranes 500A, 500B in position.

Figure 9:
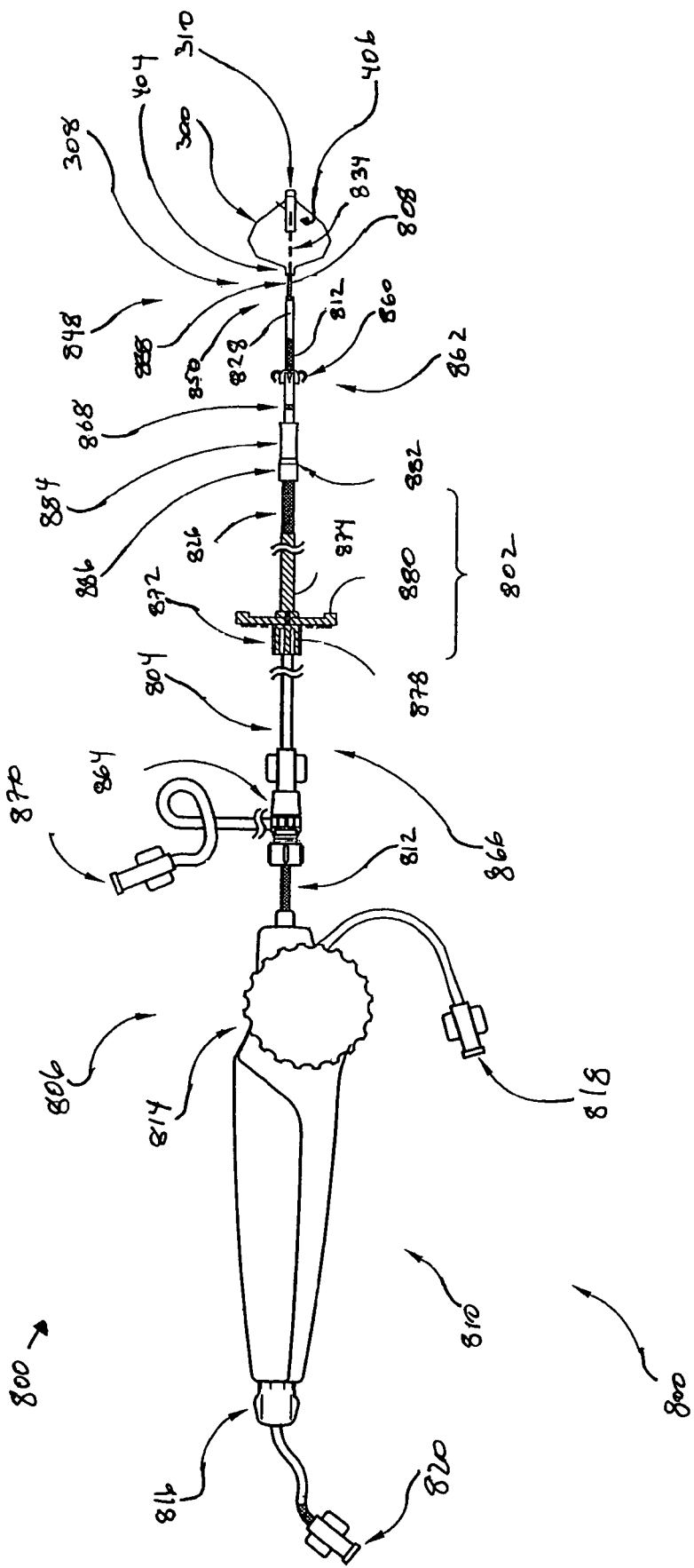

A delivery system 800 for delivering an intracardiac cage 300, particularly the cage 300 shown in FIG. 4 above, in accordance with another embodiment of the present invention is illustrated in FIGS. 8-12. Referring to FIGS. 8 and 9, the delivery system 500 preferably includes a peel-away sheath 802, a recapture sheath 804, a deployment catheter 806, and an axially moveable core 808, each described further below.

FIG. 8 illustrates the delivery system 800 without a loading collar, and FIG. 9 illustrates the deployment system with a loading collar 900. In addition, the delivery system 800 of FIG. 9 is shown with the system 800 operably connected to an intracardiac cage 300.

The deployment catheter 806 preferably comprises a deployment handle 810 and a multi-lumen shaft 812. As shown in FIGS. 8 and 9, the deployment handle 810 preferably comprises a control knob 814, a release knob 816, a proximal injection port 818 and a distal injection port 820. The multi-lumen shaft 812 preferably comprises a four-lumen shaft shown in FIG. 8A. The multi-lumen shaft 812 preferably comprises a core lumen 822 for holding an axially moveable core 808, a control line lumen 824 and two proximal injection lumens 826 in communication with the proximal injection port 818.

An axially moveable core 808 preferably extends from the deployment handle 810 through the core lumen 822 of the catheter 806 and couples the intracardiac cage 300 (not shown) to the delivery system 800 with a coupling (not shown). The coupling may be any coupling known to those of skill in the art, including a threaded portion, a lock, an interface, a grip, slider assembly 406, or any other coupling. A control line (not shown), which may be a pull wire, preferably extends through the control line lumen 824 and preferably couples the proximal hub 308 of the intracardiac cage 300 to the deployment handle control knob 814, allowing for cage 300 expansion and collapse. The control line preferably extends around a portion of the axially movable core 808 near the proximal hub 308 of the cage 300, and is coupled to the cage 300 by a crosspin 404, as shown in greater detail in FIG. 10.

Figure 10:
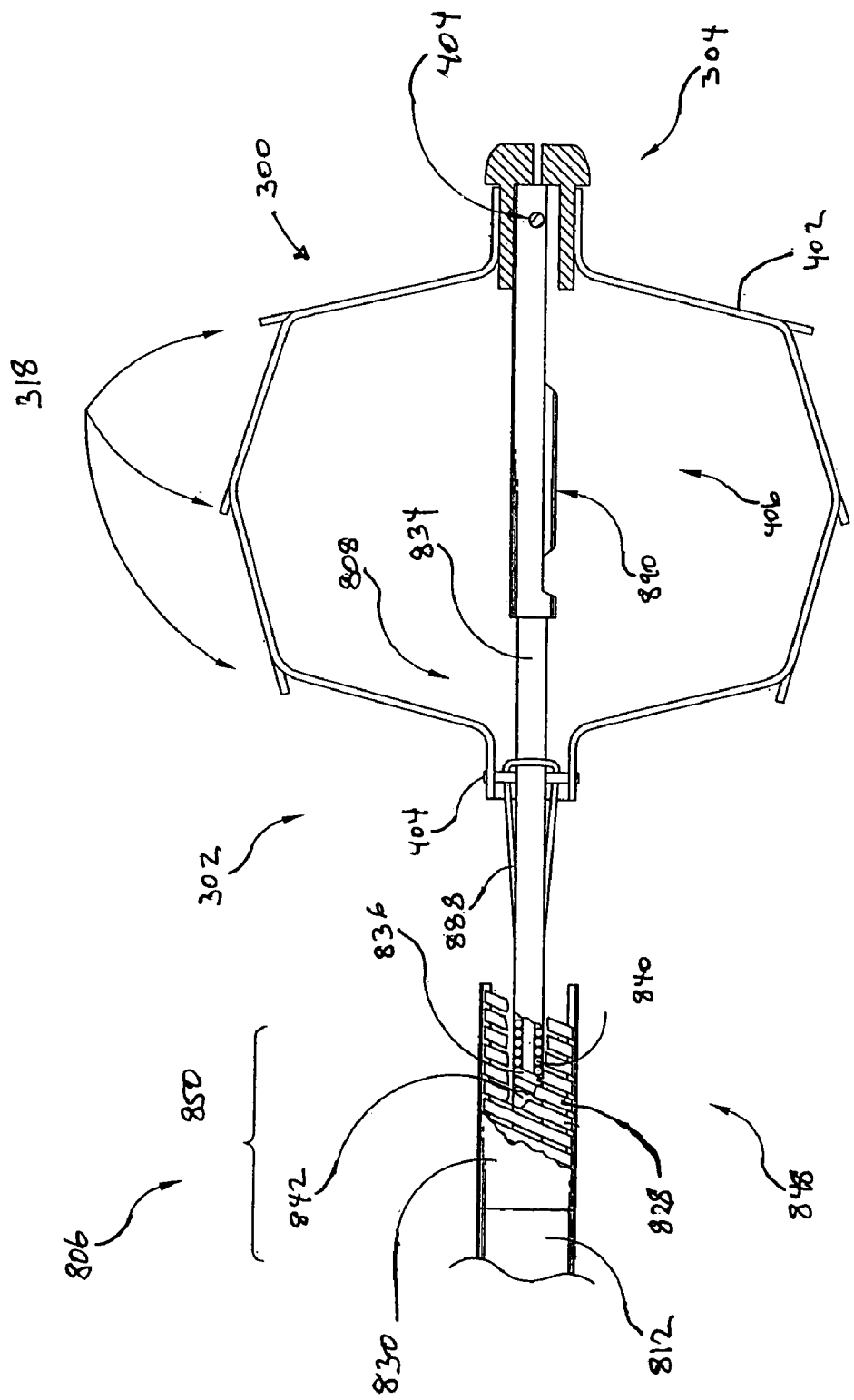
FIG. 10 is a detailed view of the distal end of the delivery system of FIG. 9.

As shown in FIG. 10, the deployment catheter 806 preferably comprises a flexible catheter section 828 at its distal end, which in some embodiments is a spiral cut tubular section housed in a polymer sleeve 830. The flexible catheter section 828 may be coupled to the distal end of the multi-lumen shaft 812.

As shown in FIGS. 10 and 11, the axially moveable core 808 preferably includes a hollow proximal shaft 832 and a hollow distal shaft 834 coupled together with a flexible hollow core section 836, all of which are co-axially aligned and connected. In one embodiment, the proximal end of the distal shaft 834 is attached to the distal end of the flexible core section 836, and the proximal end of the flexible core section 836 is attached to the distal end of the proximal shaft 832. In some embodiments, the flexible core section 836 has a spring coil section 840 housed in a polymer sleeve 842, the spring coil section 840 preferably coupled with the shafts 832, 834 at first and second ends 844, 846.

The axially moveable core 808 preferably is disposed within the deployment catheter 806 such that the flexible core section 836 may be linearly co-located with the flexible catheter section 828 at a distal portion 848 of the delivery system 800 during appropriate times during a procedure, as shown in FIG. 10. When the flexible core section 836 is aligned and linearly co-located with the flexible catheter section 828, the sections 828, 836 preferably cooperate to form a delivery system flexible segment 850. As shown in FIGS. 8-10, the delivery system flexible segment 850 preferably is located toward a distal end 848 of the delivery system 800.

In one embodiment, shown in FIG. 11, the distal shaft 834, flexible core section 836, and proximal shaft 832 are attached by welding. Small windows 852 may be provided to allow welding materials to flow between the shafts 832, 834, 836 and provide stronger bonding therebetween. In another embodiment, solder, glue, or press-fitting is used to attach the shafts 832, 834, 836 to one another, as is well known to those of skill in the art. In another embodiment, the shafts 832, 834, 836 are formed from a single tube, for example, a laser-cut tube. In other embodiments, more than one tube may be used to form each of the shafts 832, 834, 836. For example, FIG. 11 illustrates proximal shaft 832 comprising two tubes connected by welding such as described above.

Referring to FIG. 11A, distal contrast media preferably can be injected through a lumen 854 in the shafts 832, 834 for determining the placement of the intracardiac cage 300. The lumen 854 can be in fluid communication with the distal injection port 820, shown in FIGS. 8 and 9. The distal shaft 834 preferably includes a mating surface 856 and a radiopaque marker 858. In one embodiment, the mating surface 856 is a threaded surface. The distal shaft 834 preferably is releasably coupled to the intracardiac cage 300 with the slider assembly 406.

Referring back to FIGS. 8 and 9, when the delivery system 800 is assembled, the recapture sheath 804 is preferably loaded over the deployment catheter 806, distal to the handle 810. The recapture sheath 804 preferably is designed to allow recapture of the cage 300 prior to its final release, such as described with respect to retrieval catheter below. Recapture petals or flares 860 preferably are provided on the distal end 862 of the recapture sheath 804 to cover the anchors 318 of the cage 300 during retrieval of the cage 300 and re-loading of the cage 300 into the transseptal sheath (not shown), as described further below. A Touhy-Borst adapter or valve 864 preferably is attached to the proximal end 866 of the recapture sheath 804. The recapture sheath 804 preferably comprises a radiopaque marker 868 on its distal end 862 near the recapture flares 860. The recapture sheath 804 preferably comprises a recapture sheath injection port 870 for delivering fluid proximal the cage 300.

The peel-away sheath 802 preferably is provided over a portion of the recapture sheath 804, between the Touhy-Borst valve 864 and recapture flares 860. The peel-away sheath 802 preferably is used to introduce the delivery system 800 into a transseptal sheath, as described in greater detail below. As shown in FIGS. 8 and 9, the peel-away sheath 802 preferably includes a locking collar 872, a peel-away section 874, and a reinforced section 876. The locking collar 872 can be unlocked relative to the peel-away section 874, and preferably includes a threaded hub 878 that releasably engages tabs 880 of the peel-away section 874.

A loading collar 882 (shown in FIG. 9) preferably is located over a portion of the peel-away sheath 802 and a portion of the recapture sheath 804 with its proximal end located over the peel-away sheath 802 and its distal end loaded over the recapture sheath 804. The loading collar 882 preferably accommodates loading a collapsed cage 300 into the peel-away sheath 802, as described below. As shown in FIG. 9, the loading collar 882 preferably comprises a first end portion 884 adapted to receive and extend over a collapsed cage 300, and a second end portion 886 configured to guide the collapsed cage 300 into the peel-away sheath 802. The loading collar 882 preferably is made of stainless steel.

System Assembly

Figure 12:
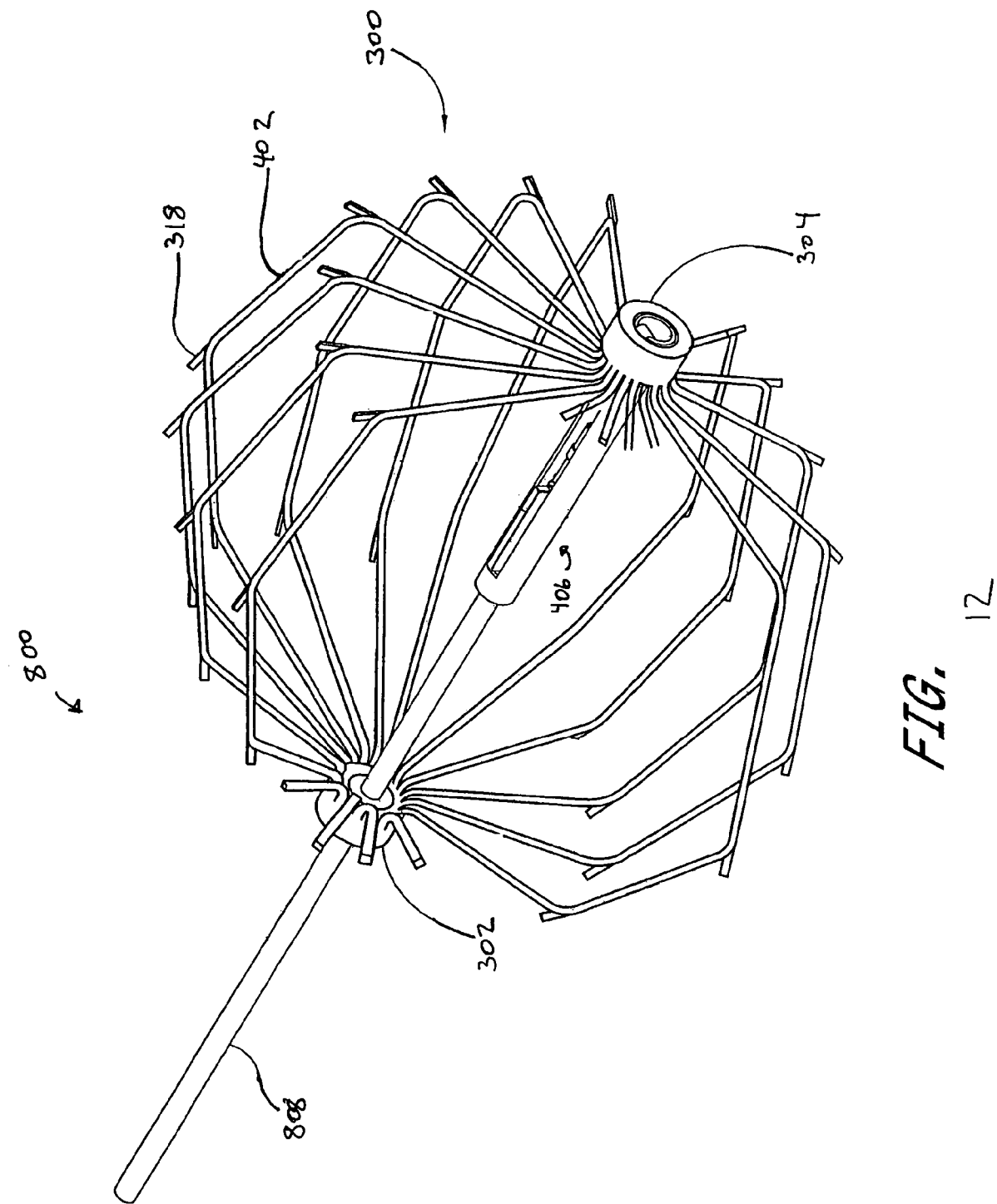
FIG. 12 is a perspective view of an intracardiac cage coupled to the axially moveable core of FIG. 11.

To assemble the delivery system 800, the axially movable core 808 and control line 888 preferably are fed into the multi-lumen shaft 812 of the deployment catheter 806. The multi-lumen shaft 812 preferably is then coupled with components of the deployment handle 810 and the injection ports 818, 820. The peel-away sheath 802 and the loading collar 882 preferably are slid onto the recapture sheath 804, and the recapture sheath 804 is slid onto the deployment catheter 806. The cage 300 preferably is then loaded on an end of the axially movable core 808 and coupled with the control line 888. In one embodiment, the cage 300 is loaded on an end of the axially movable core 808 by screwing the axially movable core 808 into the slider nut 890 of the slider assembly 406. The control knob 814 and outer casing of the deployment handle 810 preferably are then coupled with the delivery system 800. FIG. 12 illustrates one embodiment of an intracardiac cage 300 mounted to the distal end of a deployment catheter 308.

Transseptal Sheath

The delivery system 800 preferably is used in connection with a transseptal sheath 900, as illustrated in FIGS. 13A-13C, to advance the cage 300 for deployment in a patient. As shown in FIGS. 13A-13C, the transseptal sheath 900 is a tubular device that in one embodiment can be advanced over a guidewire (not shown) for accessing a chamber of a patient's heart 100. In one embodiment, the transseptal sheath 900 in one embodiment has a bend 902, as shown in FIGS. 13A and 13B. The transseptal sheath 900 of FIG. 13C is another transseptal sheath known to those of skill in the art having an enlarged diameter at its distal end. A hemostasis valve 904 is provided at the proximal end of transseptal sheath 900. A fluid injection port 906 is also provided at the proximal end to delivery fluid (such as contrast media) through the transseptal sheath 900. Systems and methods for implanting the cage 300 in a patient's heart 100 are described in greater detail below.

Crossing the Interatrial Septum

In some cases, a hole or defect exists in the atrial septum 216 of the heart 100. The hole or defect may be used in certain embodiments of the present invention to deliver an intracardiac cage 300 to the left atrium 104 of the heart 100. In such embodiments, a delivery system 800 is directed through the hole or defect from the right atrium 114 to the left atrium 104. In other cases, it is clinically indicated to pierce the septum 216 of the heart 100 with a suitable device, such as a dilator, as will be discussed in greater detail below with respect to FIGS. 14-15N.

In one embodiment, a guidewire (not shown) preferably is used to access the superior vena cava 202 through groin access. A transseptal sheath 900 preferably is advanced over the guidewire and into the superior vena cava 202. The guidewire preferably is removed and replaced with a transseptal needle (not shown). The transseptal sheath 900 preferably is retracted inferiorly so that the bend 902 in the transseptal sheath 900 directs the distal tip of the transseptal sheath 900 toward the fossa ovalis. The needle preferably is advanced to puncture the fossa ovalis. The transseptal sheath 900 preferably is advanced to establish access to the left atrium 104 and the needle preferably is retracted. Further details or disclosure are provided in copending U.S. Patent Applications No. 09/435,562, filed Nov. 8, 1999 and 10/033,371, filed Oct. 19, 2002, published as U.S. Publication No. 2002/0111647, the entireties of which are hereby incorporated by reference.

Dilator

FIGS. 14 and 14A show a dilator 910 in accordance with one embodiment of the present invention for accessing the left atrium 104 of the heart 100 via the right atrium 114. The dilator 910 has a proximal end 912, a distal end 914, and an elongate flexible tubular body 916. The overall length of the dilator 910 depends upon the percutaneous access point and the desired application. For example, lengths in the area of from about 80 cm to about 100 cm are typical for use in percutaneous transluminal access at the femoral vein for locating and puncturing a site on the atrial septum in the heart.

The tubular body 916 may be manufactured in accordance with any of a variety of known techniques, for manufacturing catheters adapted to reach the coronary arteries or chambers of the heart. For example, the tubular body 916 may be manufactured as an extrusion of appropriate biocompatible polymeric materials such as high/low density polyethylene (HDPE/LDPE), polytetrafluoroethylene (PTFE), nylons, and a variety of others which are known in the art. Blended materials may also be used, such as HDPE (e.g., HDPE/LDPE ratios such as 50%:50%, 60%:40% and others) with from about 5% to about 25%, and, in one embodiment, about 20% $BaSO_4$ for lubricity and radiopacity. Alternatively, at least a portion or all of the length of tubular body 916 may comprise a spring coil, solid walled hypodermic needle tubing (e.g., stainless steel, NiTi alloys) or braided reinforced wall as is understood in the catheter and guidewire arts.

For most applications, the tubular body 916 is provided with an approximately circular cross sectional configuration having an outside diameter within the range of from about 0.020" to about 0.300". In accordance with one embodiment of the invention, the tubular body 916 has an outside diameter of about 0.160" throughout its length. Other lengths and diameters may be readily utilized, depending upon the desired profile and performance characteristics.

The proximal end 912 is provided with a manifold 918, having one or more access ports as in known in the art. In the illustrated embodiment, manifold 918 is provided with a core wire port 920 which may also or alternatively function as a guidewire port in an over the wire embodiment. An injection port 922 may also be provided, for injecting a contrast media, such as to confirm that the distal end 914 has traversed the intraatrial septum 216. Additional access ports may be provided as needed, depending upon the functional capabilities of the catheter. The manifold 918 may be injection molded from any of a variety of medical grade plastics or formed in accordance with other techniques known in the art.

The flexible body 916 is provided with a preset bend 924, for assisting in biasing the distal end 914 against the intraatrial septum 216 as is understood in the art. The bend 924 preferably has a radius within the range of from about 0.5 cm to about 5 cm and, in one embodiment, about 2.5 cm. The bend 924 is centered on a point which is within the range of from about 1 cm to about 10 cm proximally from distal end 914. In one embodiment, the bend 924 is centered at approximately 6 cm proximally from distal end 914. The bend 924 can be defined by a proximal transition where it meets the substantially linear proximal portion of the dilator 910, and a distal transition where it meets the substantially linear distal portion of the dilator 910. The angular deflection of the bend 924 is generally within the range of from about 30° to about 80° and, in one embodiment, is about 50°.

The bend 924 may be provided in accordance with any of a variety of techniques. For example, when the tubular body 916 includes a hypotube or other metal tubing, it may be bent such as around a forming mandrel in excess of the elastic limit of the hypotube. Alternatively, an injection molded catheter body may be heat set in a predetermined bend, such as with removable flexible mandrels extending through any interior lumen to maintain patency of the lumen around the bend 924. Other techniques will be known to those of skill in the art. Alternatively, the bend 924 may be formed during or after placement of the catheter in the heart. This may be accomplished by providing the dilator 910 with any of a variety of steering mechanisms, which allow a distal portion 914 of the dilator 910 to be inclined away from the axis of the normal bias of the dilator 910. For example, one or more axially moveable pull wires may extend throughout the length of the dilator 910. Proximal traction on a pull wire that is secured at the distal end 914 of the dilator 910 will cause a lateral defection of the dilator 910.

The dilator 910 is additionally provided with a tissue piercing structure 926 such as a needle 928. The needle 928 preferably includes a tubular structure such as a stainless steel hypotube having a sharpened distal end 930. The sharpened distal end 930 of the needle 928 is axially moveable and advanceable through an aperture 932 in the distal end 914 of the tubular body 916.

In one embodiment, the needle 928 has an axial length of from about 1 cm to about 5 cm, an inside diameter of about 0.022 inches and an outside diameter of about 0.032 inches. Any of a variety of other dimensions for needle 928 may also be used depending upon the desired performance and overall catheter dimensions. The needle 928 is coupled to a control element such as core wire 934 which axially moveably extends throughout the length of tubular body 916. The proximal end of the core wire 934 in the illustrated embodiment extends proximally from the core wire port 920. The needle 928 is preferably axially moveable between a first position in which the tip 930 is contained within the distal end 914 of the tubular body 916 and a distal position in which the tip 930 of the needle 928 is exposed beyond the distal end of the tubular body 916, such as for piercing the fossa ovalis. Distal advancement of the proximal end of the core wire 934 will advance the needle 928 from the first position to the second position as will be appreciated in view of the disclosure herein. In addition, the needle 928 and core wire 934 may be removed entirely from the dilator 910, except when desired to pierce the septum. Other mechanisms known to those of skill in the art, such as spring-loaded needles with trigger releases, may be used to move the needle 928 from the first position to the second position.

Once the piercing structure 926 has pierced the fossa ovalis or other structure, and the distal end 914 of the dilator 910 is advanced through the opening formed by the piercing structure, the piercing structure 926 may be proximally retracted and removed from the dilator 910, thereby leaving the central lumen of the dilator 910 fully available for subsequent therapeutic or diagnostic devices or materials.

Preferably, the distal end 914 of the dilator 910 is provided with a tapered frustro conical surface 936. This allows the tubular body 916 to function as a dilator, thereby permitting the tapered surface 936 to enlarge the opening formed by needle 928 while minimizing "tenting" of the fossa ovalis during a transseptal access procedure.

Piercing the Interatrial Septum

Figure 15A:
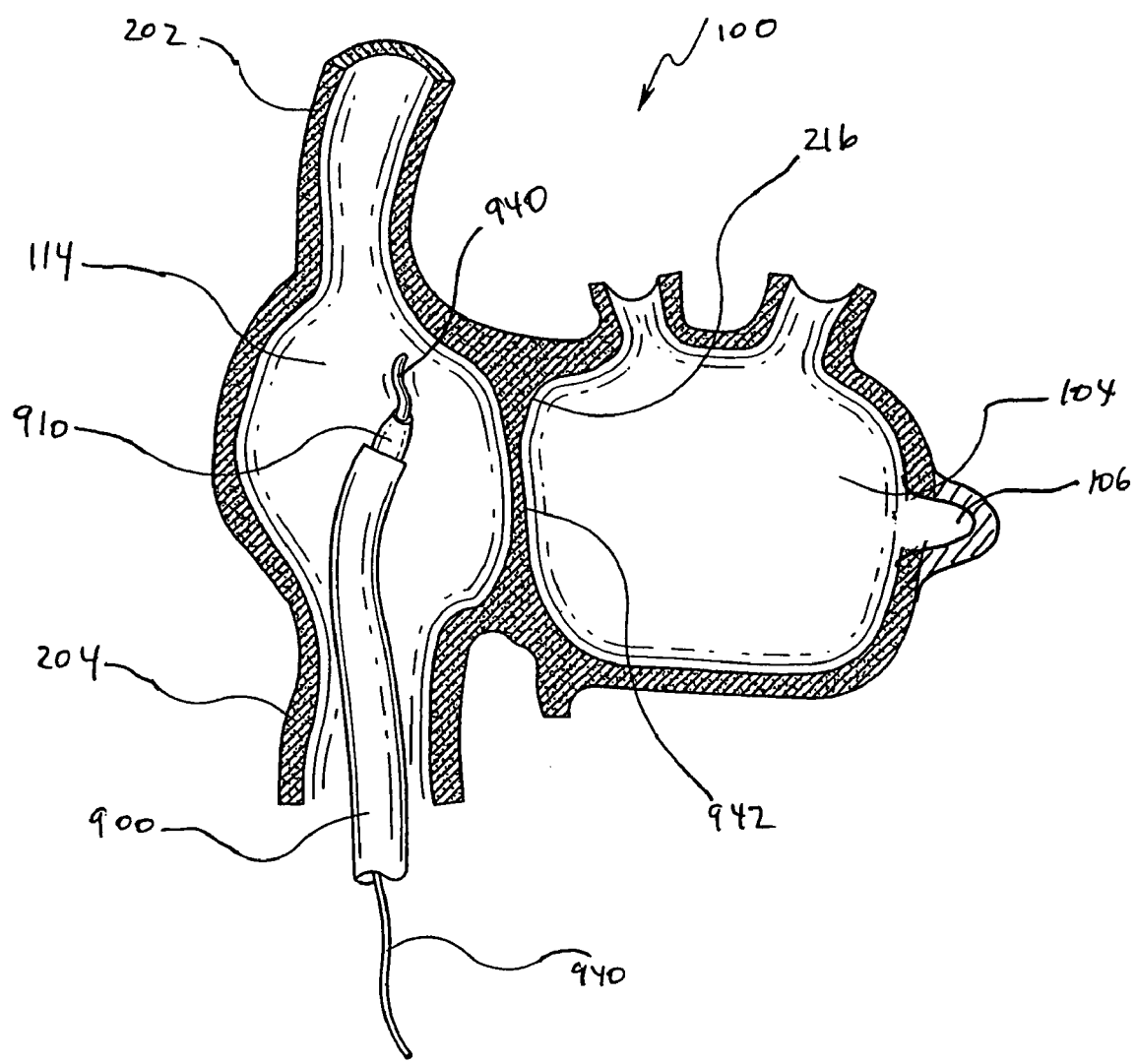
FIGS. 15A-15N are schematic, partial cross-sectional views showing the delivery and deployment of an intracardiac cage to the left atrium of a patient's heart.
Figure 15B:
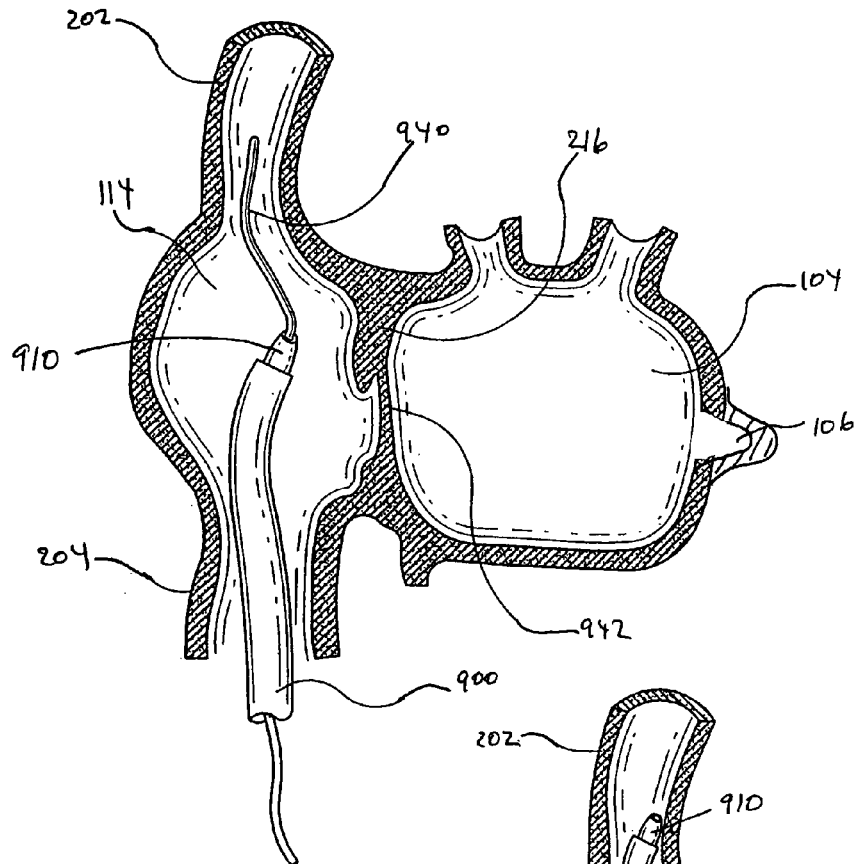
Figure 15C:
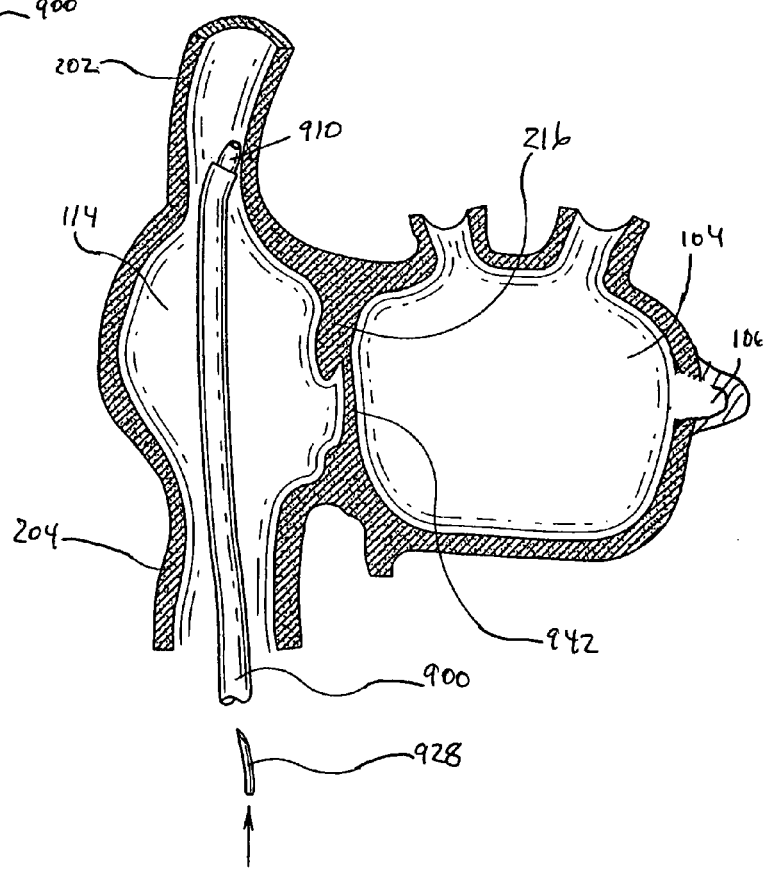
Figure 15D:
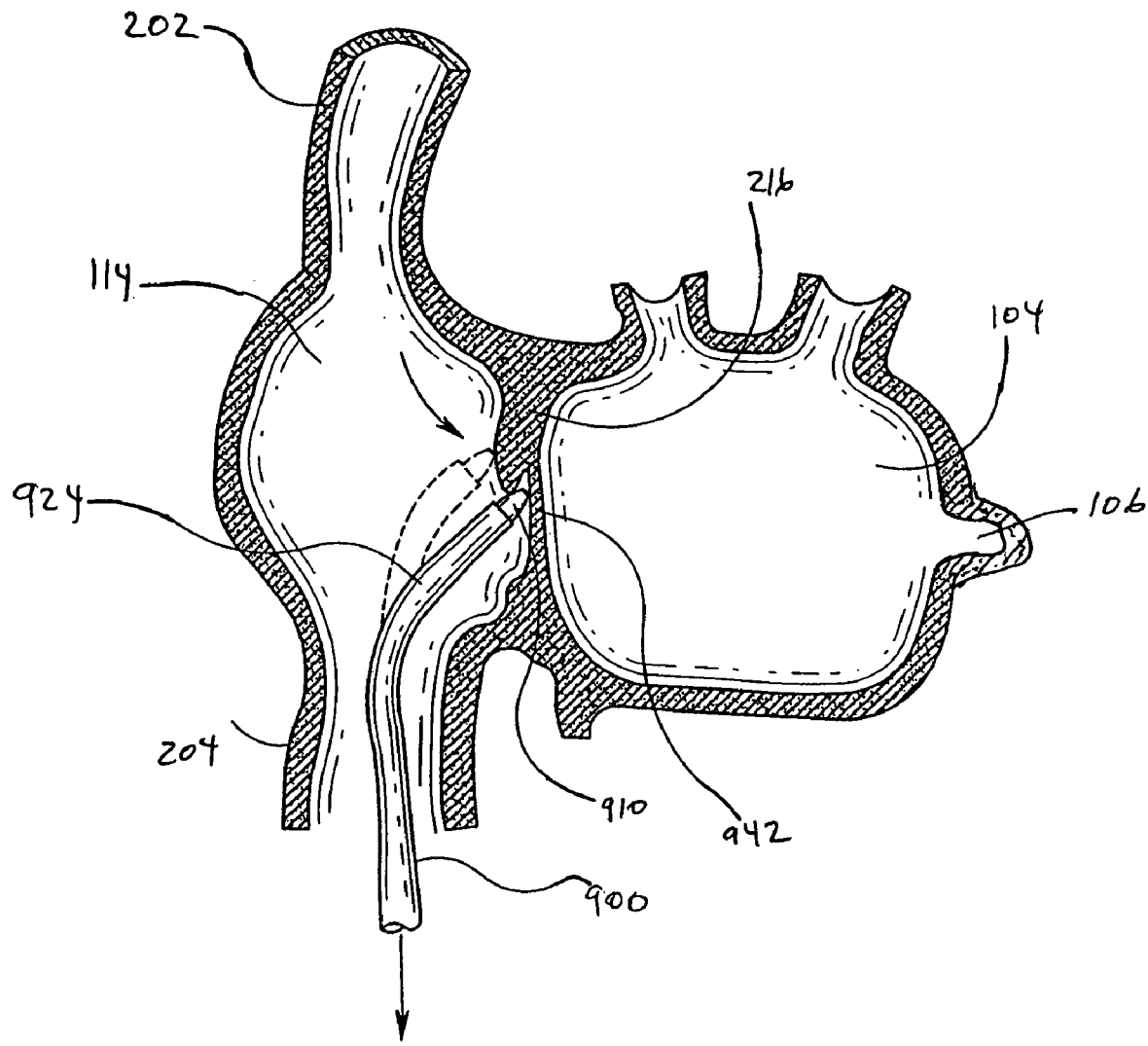
Figure 15F:
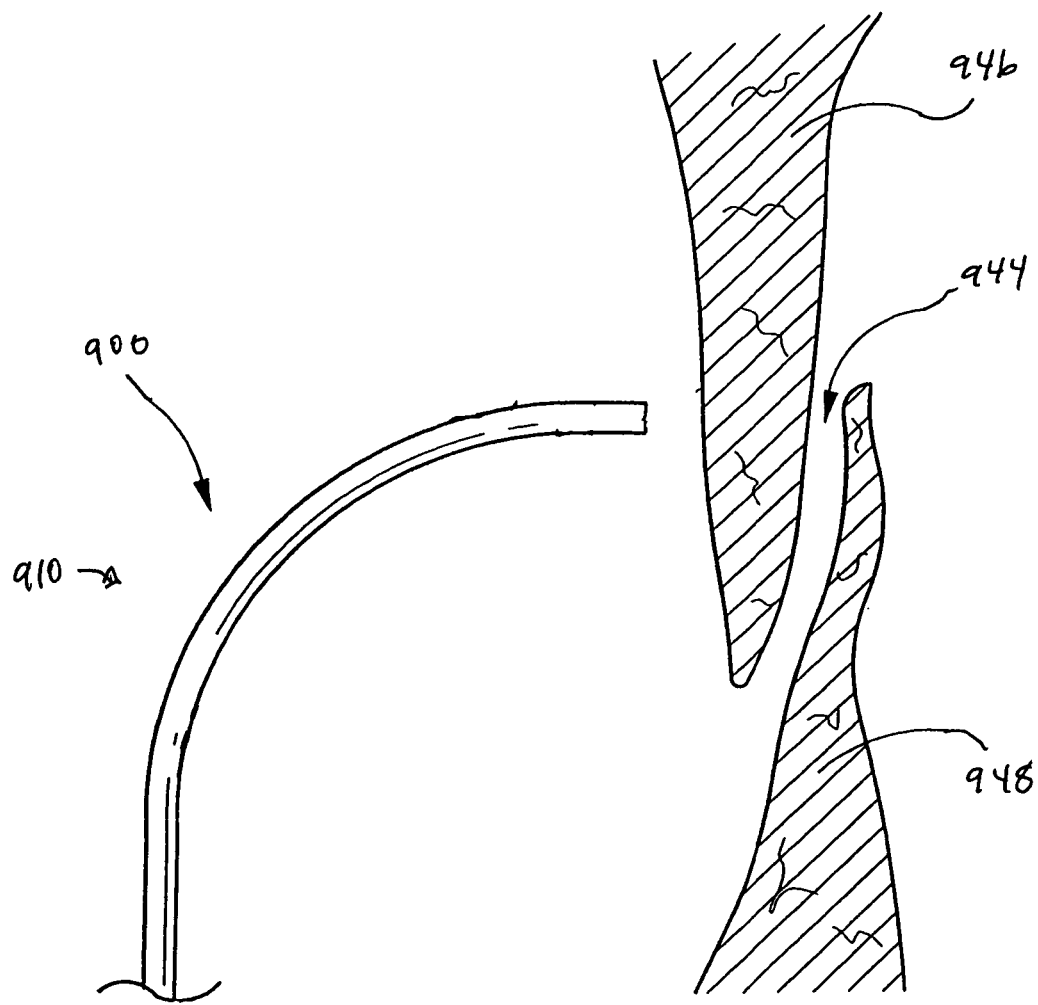
Figure 15G:
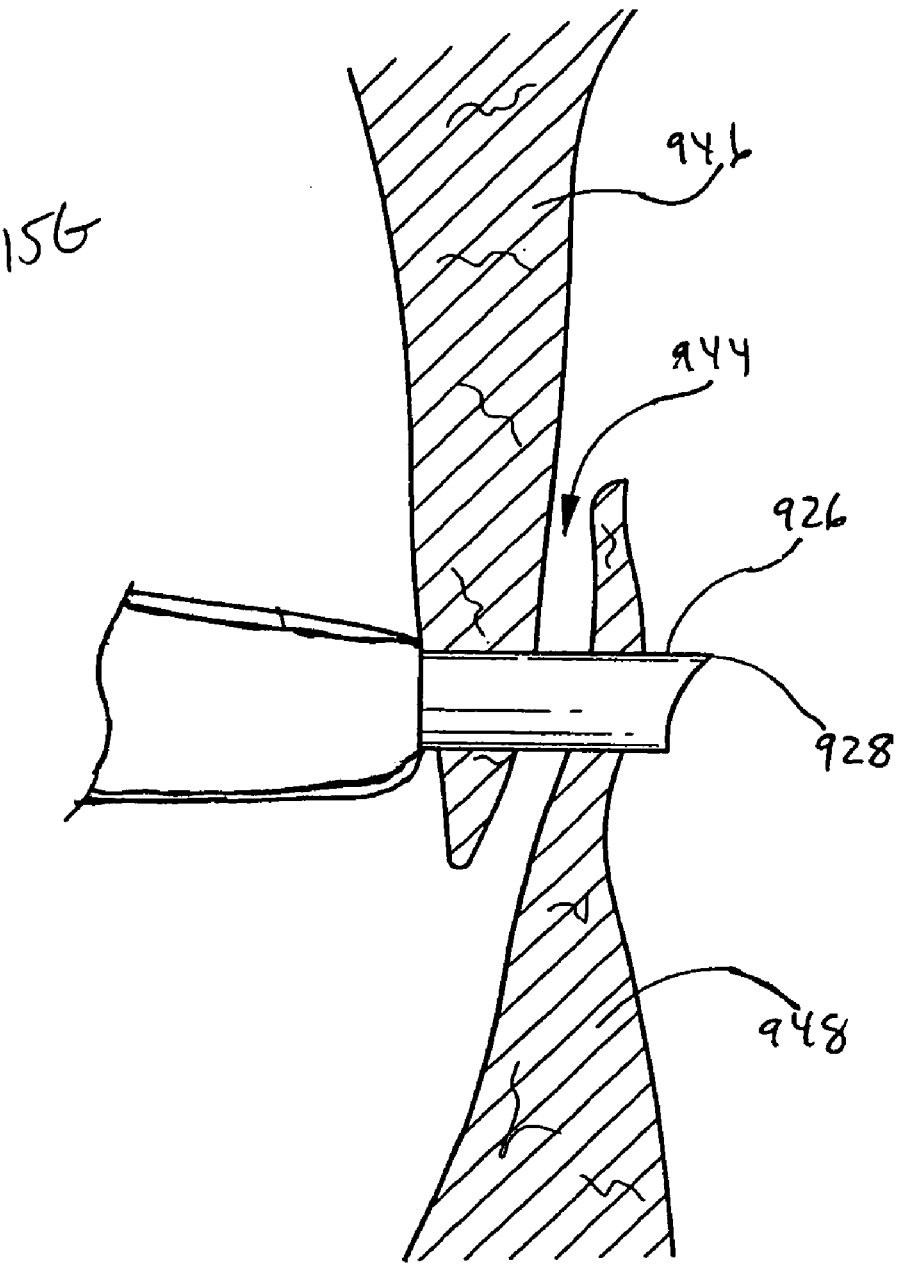
Figure 15E:
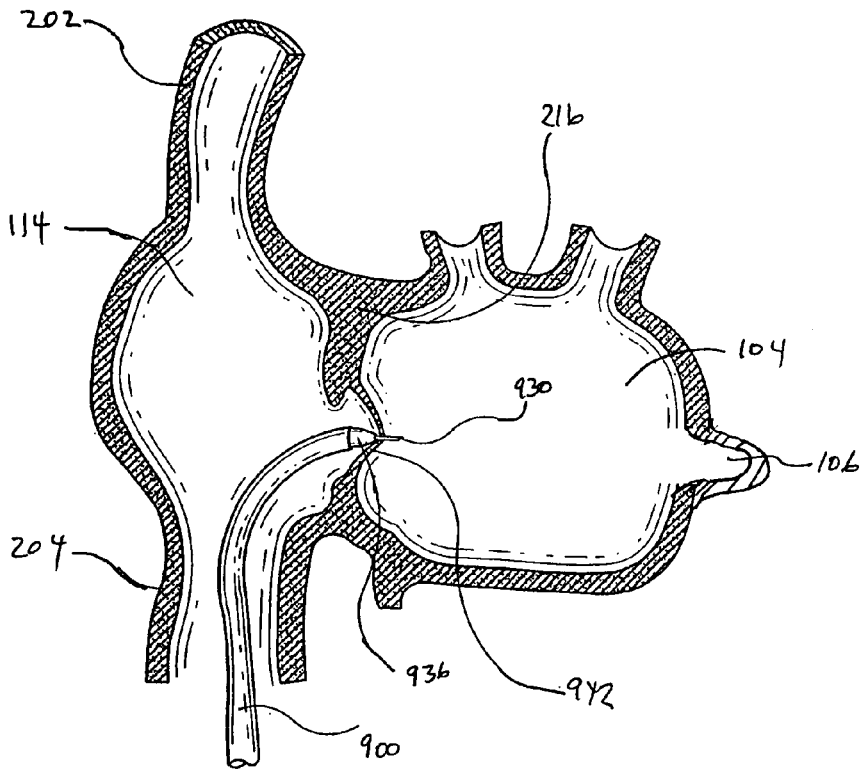
Figure 15H:
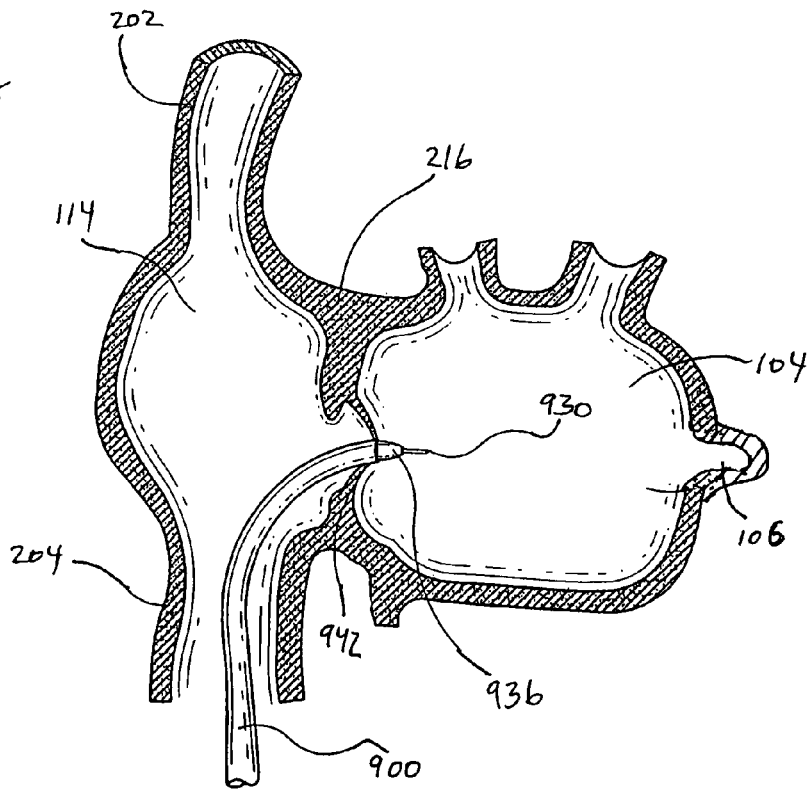
Figure 15:
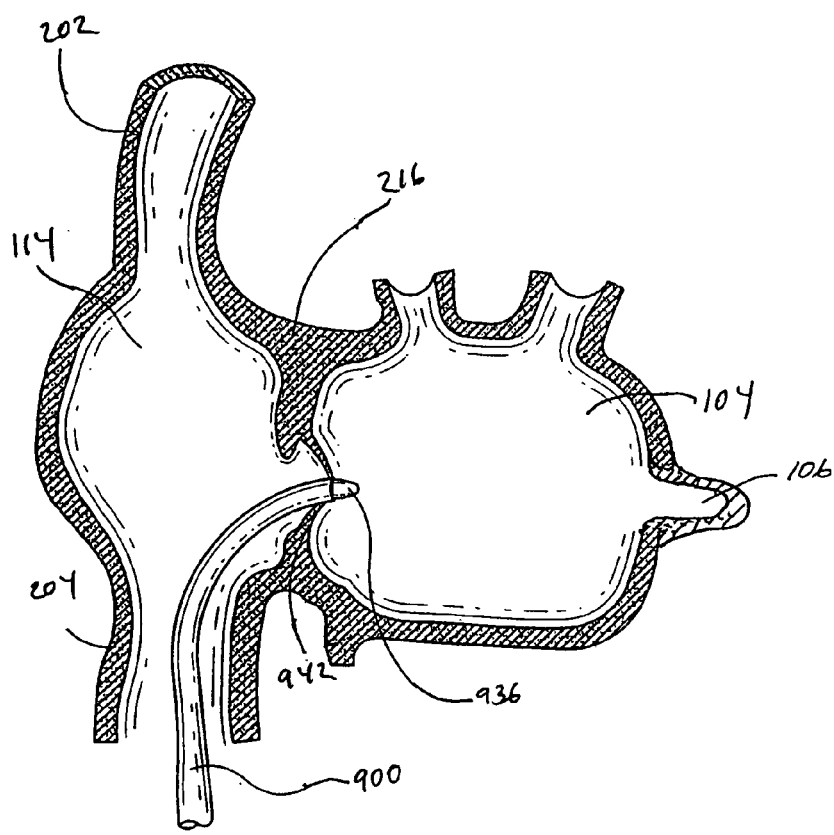
Figure 15:
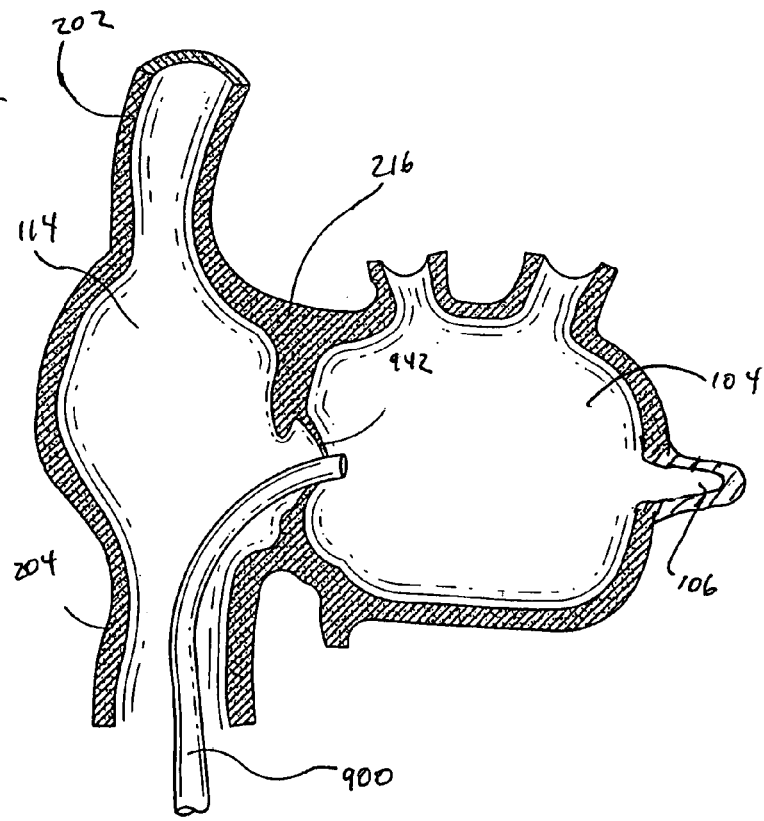
Figure 15K:
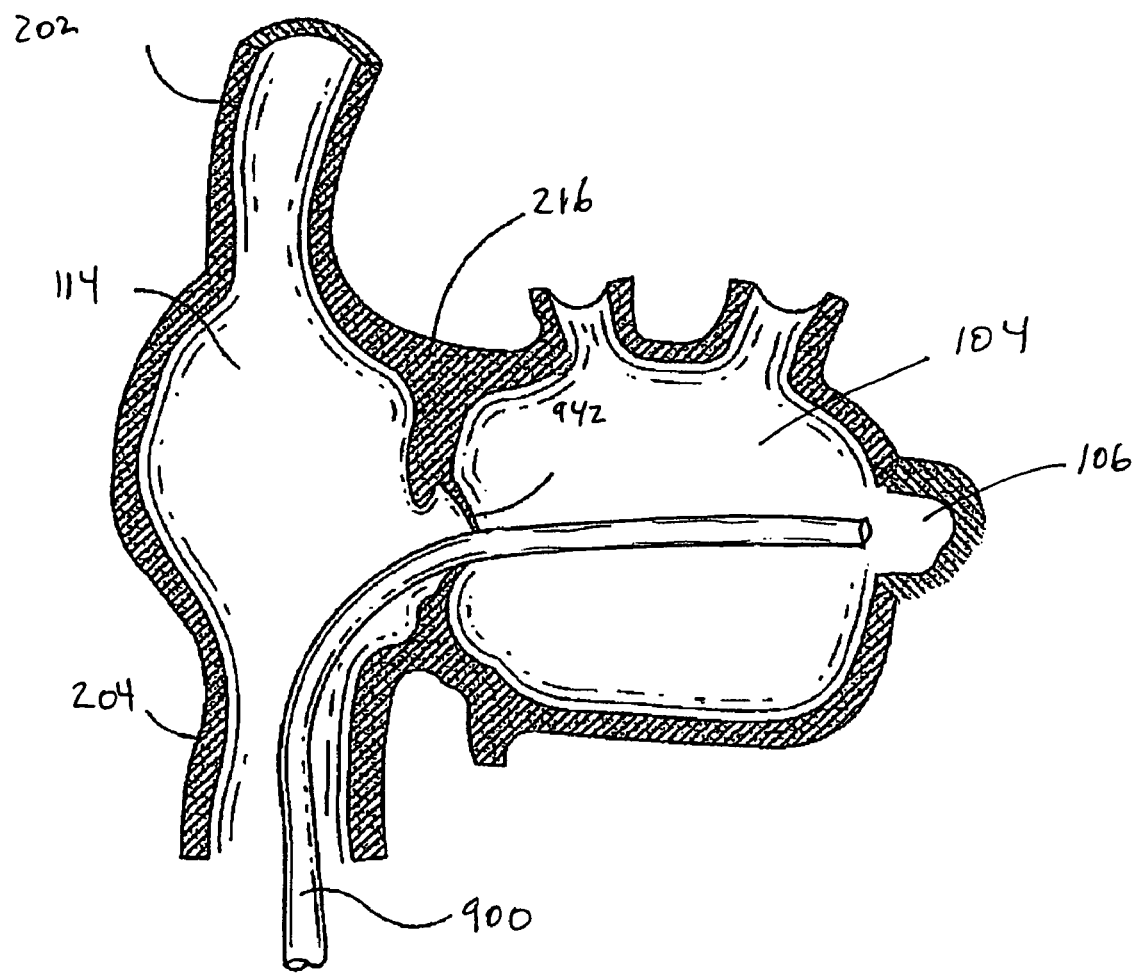
Figure 15L:
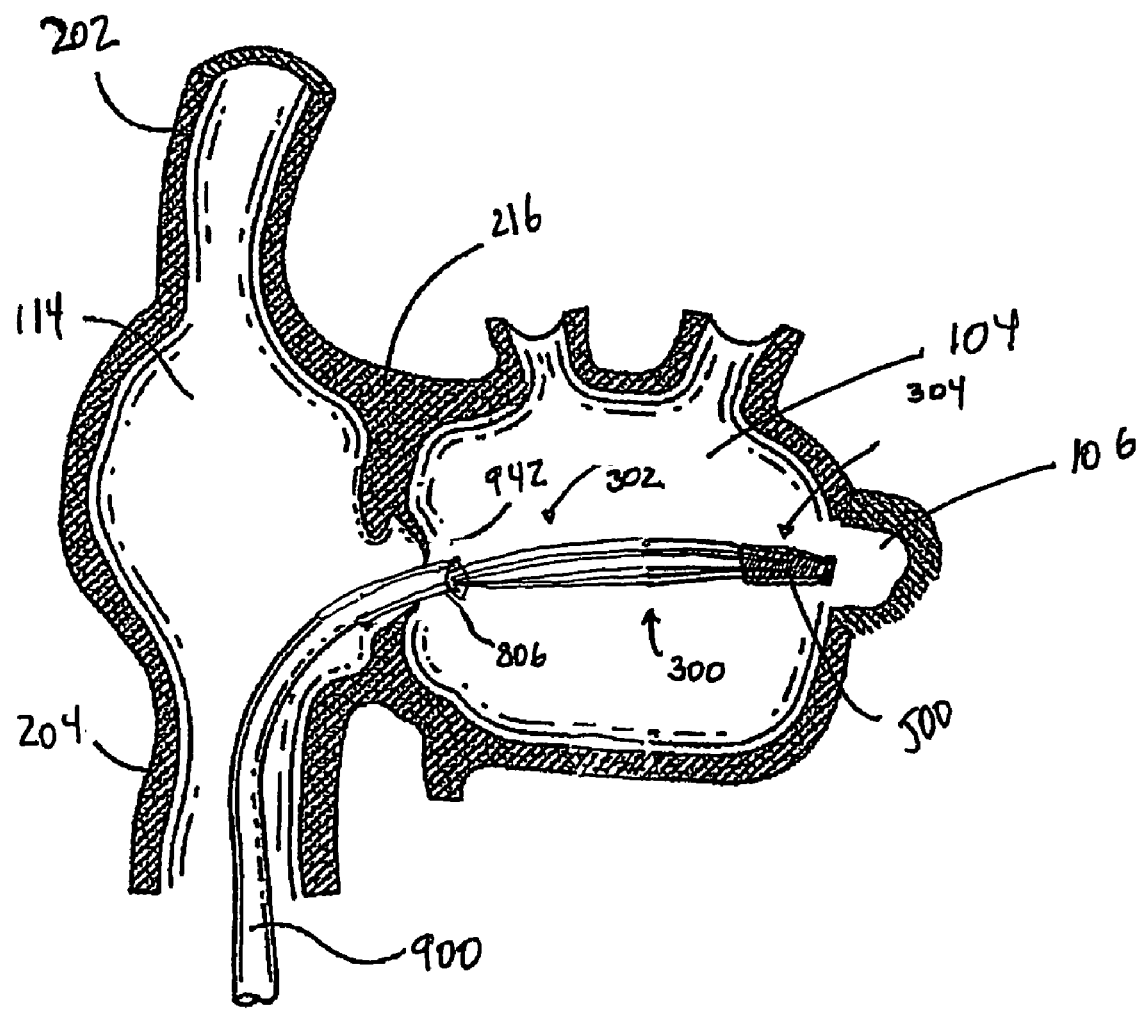
Figure 15M:
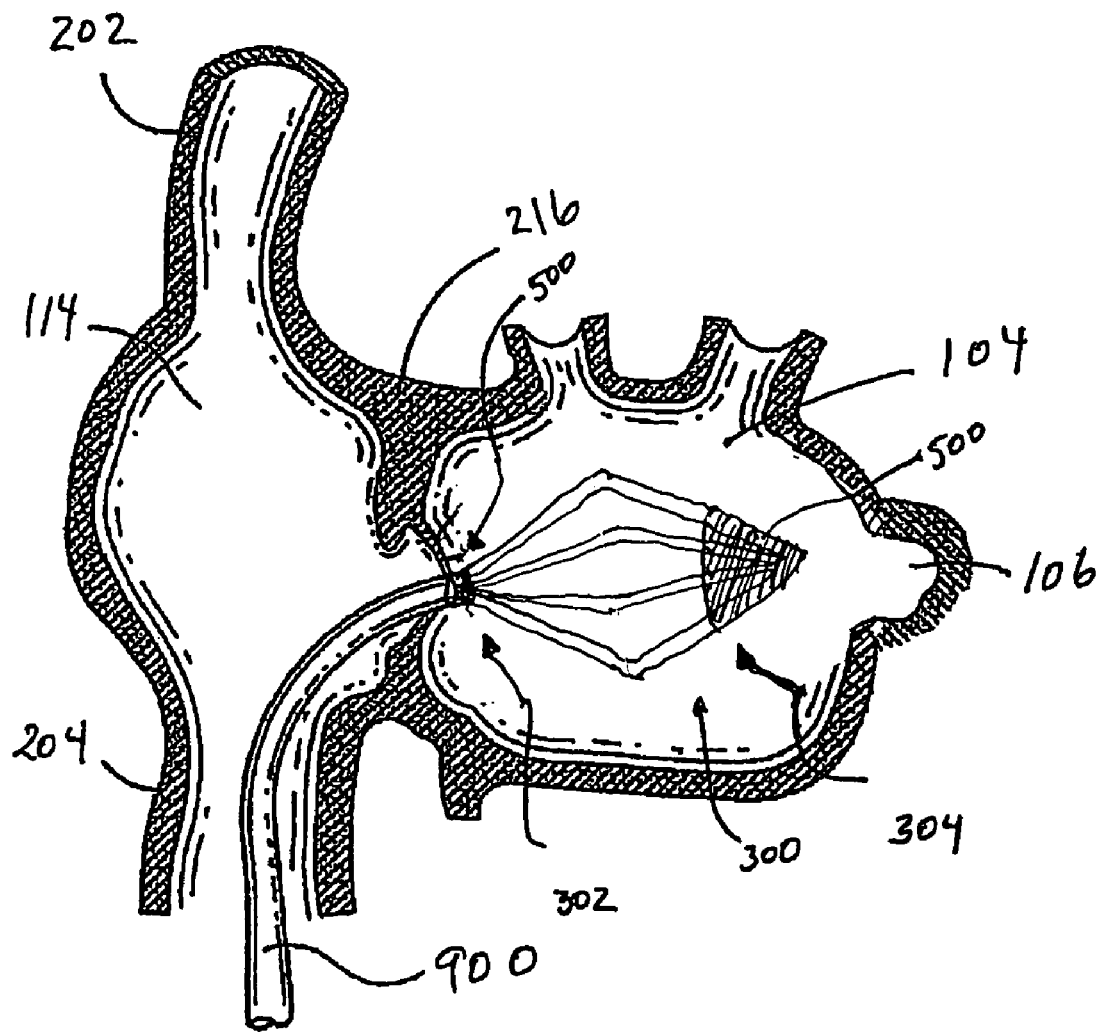
Figure 15N:
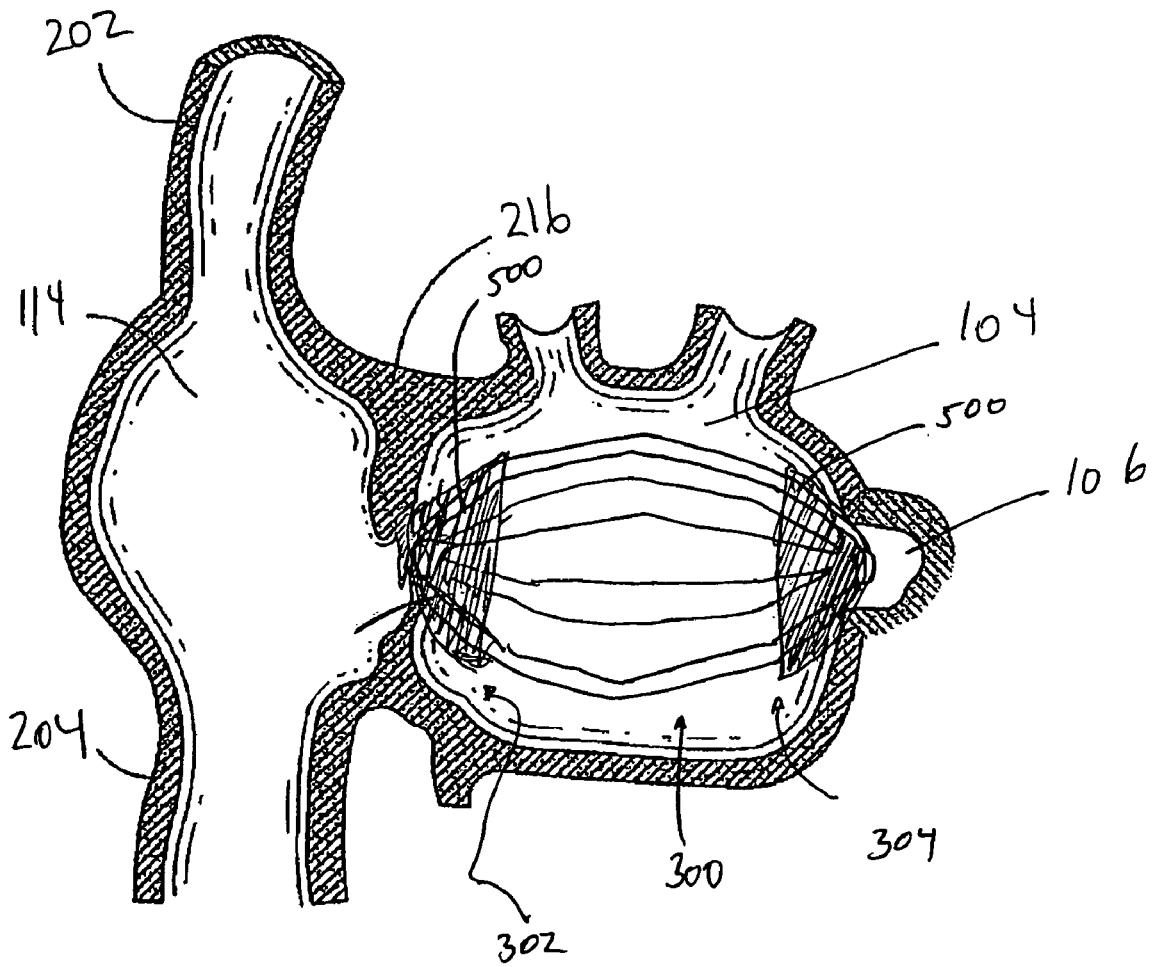

In accordance with embodiments of the present invention as illustrated in FIGS. 15A-15N, the right atrium 114 may be initially accessed with a transseptal access system through either the inferior or superior vena cava 204, 202, which initially involves cannulation with an introducer sheath such as through the well known "Seldinger" technique. A transseptal access system of the present invention includes a transseptal sheath 900, a piercing dilator catheter 910 as discussed above, and an appropriately sized guidewire 940.

One access point is along the right femoral vein, although access from the left femoral vein is also possible. Access may also be achieved through a puncture in any of a variety of other veins of suitable internal diameter and the present invention is not limited in this regard.

A conventional spring tipped guidewire 940 is thereafter advanced through the needle into the vein and the needle is subsequently removed. The dilator 910 is positioned within a sheath such as a 14 French introducer sheath. Subsequently, the sheath and inner dilator 910, in combination with the guidewire 940, are advanced through the femoral vein to the right atrium 114.

FIG. 15A illustrates a schematic partial cross-section of a portion of the heart 100. The right atrium 114 is in communication with the inferior vena cava 204 and the superior vena cava 202. The right atrium 114 is separated from the left atrium 104 by the interatrial septum 216. The fossa ovalis 942 is located on the interatrial septum 216. As seen in FIG. 15A, the sheath 900 having the dilator 910 and guidewire 940 therein are initially positioned within the right atrium 114.

The guidewire 940 is then distally advanced to access the superior vena cava 202, as shown in FIG. 15B. The dilator 910 and sheath 900 are advanced into the superior vena cava 202, as illustrated schematically in FIG. 15C. The guidewire 940 is proximally retracted.

When the sheath 900 and dilator 910 are in the superior vena cava 202 and the guidewire 940 has been removed, the transseptal needle 928 is advanced through the central lumen of the dilator 910 and sheath 900. The transseptal needle 928 is advanced (possibly with a stylet in place) to a point that the stylet tip is just inside the distal tip of the sheath 900 and dilator 910, a position previously noted by the operator, and the stylet is withdrawn from the transseptal needle 928.

The remaining combination of the sheath 900 with the dilator 910 having the transseptal needle 928 therein, is then drawn proximally from the superior vena cava 202 while the preset curves 902, 924 at the distal region of sheath 900 and dilator 910 cause the tip of the sheath-dilator-transseptal needle combination to "drag" along the wall of the right atrium 114 and septum 216, as shown in FIG. 15D, until the desired penetration location, such as the fossa ovalis 942, is reached.

The tip of the dilator 910 is then positioned against the septum 216 by distal advancement through the sheath 900. The tip is then dragged along the septum 216 by proximal traction on the dilator 910 until the tip pops onto the fossa ovalis 942. Various methods and devices known to those of skill in the art may be utilized to help identify the location of the fossa ovalis. 942. One such method and device is described in U.S. application Ser. No. 10/100,270, filed, Mar. 15, 2002, published as U.S. Publication No. 2002/0169377, which is incorporated by reference herein.

The physician is normally assisted during placement, as in the entire procedure, by fluoroscopy or other visualization techniques. To assist in such visualization, the distal tip of sheath 900 and the distal tip of dilator 910 may be provided with a radiopaque marker. In addition, some physicians find it desirable to infuse a radiopaque dye through the transseptal needle 928 at various stages of the procedure to assist in visualization, particularly following the transseptal puncture.

After the tip of the sheath-dilator-transseptal needle combination has been placed in the desired location against the fossa ovalis 942, the transseptal needle 928 is abruptly advanced to accomplish a quick puncture, as illustrated in FIG. 15E. Immediately after the puncture, one medical technique is to confirm the presence of the tip 930 of the transseptal needle 928 within the left atrium 104. Confirmation of the location of the tip 930 of the transseptal needle 928 may be accomplished by monitoring the pressure sensed through the transseptal needle lumen to ensure that the measured pressure is within the expected range and has a waveform configuration typical of left atrial pressure. Alternatively, proper position within the left atrium 104 may be confirmed by analysis of oxygen saturation level of the blood drawn through the transseptal needle 928; e.g., aspirating fully oxygenated blood. Finally, visualization through fluoroscopy alone, or in combination with the use of dye, may also serve to confirm the presence of the tip 930 of the transseptal needle 928 in the left atrium 104.

Alternatively, if the septum 216 includes a hole or defect, such as a patent foramen ovale, the method of the embodiment illustrated in FIGS. 15F-15G may be used. Referring to FIG. 15F, a sheath 900 that includes a dilator 910 (not shown) is positioned adjacent the patent foramen ovale 944. The patent foramen ovale 944 generally includes a septum secundum 946 and a septum primum 948. Additional devices and methods for piercing the septum primum and secundum are shown in U.S. application Ser. No. 10/972,635, filed Oct. 25, 2004, published as U.S. Publication No. 2005/0119675, which is incorporated by reference in its entirety.

The transseptal sheath 900 and dilator 910 are positioned adjacent to the patent foramen ovale 944 and its tissue piercing structure 926 is advanced distally through the septum secundum 946 and septum primum 948 by actuating an actuator, such as a control on the dilator 910 manifold 918. In some embodiments, the tissue piercing structure 926 may be advanced across the septa manually. In other embodiments, tissue piercing structure 926 may be advanced across the septa using a spring loaded handle. Crossing the septa quickly using a spring loaded handle may facilitate crossing of the septum primum 948.

After placing the transseptal needle tip 930 within the left atrium 104, the tip 936 of the dilator 910 is advanced through the septum 216 and into the left atrium 104, as shown in FIG. 15H. Typically, care is taken to ensure that, at the same time of advancing the dilator 910 and sheath 900 into the left atrium 104, the tip 930 of the transseptal needle 928 is not advanced a sufficient distance such that the needle 928 can damage the inside wall of the left atrium 104. When the tapered tip 936 of the dilator 910 appears to have entered the left atrium 104, the transseptal needle 928 is withdrawn. The sheath 900 is then advanced into the left atrium 104, either by advancing the sheath 900 alone over the dilator 910 or by advancing the sheath 900 and dilator 910 in combination, as shown in FIG. 15I. The dilator 910 is then withdrawn from sheath 900, as shown in FIG. 15J. The main lumen of the sheath 900 is now available as a clear pathway to advancing further diagnostic or therapeutic instruments into the left atrium, such as the delivery system 800 described in greater detail above with respect to FIGS. 8-12.

After preparing a transseptal sheath 900 for left atrial 104 access, the size and morphology of the left atrium 104 can be determined by injecting contrast media through the sheath 900 and into the left atrium 104.

In one embodiment, the system and method preferably allows for selection and preparation of a deployment system 800. The delivery system 800 preferably comprises an intracardiac cage 300 of an appropriate size for placement in a patient. Initially, the cage 300 preferably is in an expanded configuration, with its axially moveable core 808 engaging a slider assembly 406, as described above. A recapture sheath 804 preferably is positioned so it covers and supports the flexible segment 850 of the delivery system 800, wherein the flexible catheter section 828 of deployment catheter 806 and flexible core section 836 of axially moveable core 808 are aligned. The Touhy-Borst valve 864 preferably is tightened over the deployment catheter 806 to prevent relative movement between recapture sheath 804 and deployment catheter 806. The loading collar 882 and peel-away sheath 802 preferably are positioned so they are at the base of the recapture flares 860, proximal thereto.

The delivery system 800 preferably is loaded by rotating the control knob 814 counterclockwise until the cage 300 is fully collapsed. Preferably, at least a portion of the control line 888 is coupled with the control knob 814 such that rotation of the control knob 814 in the counterclockwise direction retracts at least a portion of the control line 888. Retraction of the control line 888 preferably places tension on the proximal hub 308 of the cage 300 because a portion of the control line 888 preferably is coupled with the proximal hub 308 by a pin 404. While the distal portion of the axially moveable core 808 engages the slider assembly 406 and applies a distal force to distal hub 310 of the cage 300, tension in the control line 888 preferably causes the proximal hub 308 of the cage 300 to move proximally relative the axially moveable core 808, thereby collapsing the intracardiac cage 300.

The diameter of the cage 300 preferably is reduced to approximately $\frac{1}{3}^{rd}$ or less of its original diameter when collapsed. The loading collar 882 and peel-away sheath 802 are then advanced distally over the flares 860 and cage 300 until the distal tip of the cage 300 is aligned with the distal end of the peel-away sheath 802 and the distal end of the loading collar 882 is about 1.5 cm from the distal tip of the cage 300. At this point, the flares 860 partially cover the cage 300. The loading collar 882 preferably is removed and discarded.

With the cage 300 partially within the recapture sheath 804 and retracted within the peel-away sheath 802, the entire system preferably is flushed with sterile heparinized saline after attaching stopcocks to the recapture sheath injection port 870, the proximal injection port 818 and distal injection port 820 of the delivery system 800. The recapture sheath 804 and the Touhy-Borst valve 864 are first thoroughly flushed through port 870. The distal injection port 818 and the proximal injection port 820 of the deployment handle 810 are preferably flushed as well. The distal injection port 820 is in fluid communication with lumen 854 of the axially moveable core 808, and the proximal injection port 818 is in fluid communication with injection lumens 826 of the multi-lumen shaft 812. The transseptal sheath 900 placement preferably is reconfirmed using fluoroscopy and contrast media injection.

The delivery system 800, as described above, with the cage 300 coupled thereto, preferably is then inserted into the proximal end of the transseptal sheath 900. To avoid introducing air into the transseptal sheath 900 during insertion of the delivery system 800, a continual, slow flush of sterile heparinized saline preferably is applied through the proximal injection port 818 of the deployment handle 810 to the distal end of the deployment catheter 806 until the tip of the peel-away sheath 802 has been inserted into, and stops in, the hemostatic valve 904 of the transseptal sheath 900. Preferably, the distal tip of the peel-away sheath 802 is inserted approximately 5 mm relative to the proximal end of the transseptal sheath 900.

Under fluoroscopy, the recapture sheath 804 and deployment catheter 806 preferably are advanced, relative to the peel-away sheath 802, approximately 20-30 cm from the proximal end of the transseptal sheath 900, and the system 800 preferably is evaluated for trapped air. The peel-away sheath 802 is preferably not advanced into the transseptal sheath 900 due to the hemostasis valve 904 blocking its passage. If air is present in the system 800, it may be removed by aspirating through the distal injection port 820, recapture sheath injection port 870, or proximal injection port 818. If air cannot be aspirated, the deployment catheter 806 and recapture sheath 804 preferably are moved proximally and the delivery system 800 preferably is removed from the transseptal sheath 900. All air preferably is aspirated and the flushing/introduction procedure preferably is repeated.

The peel-away sheath 802 preferably is manually slid proximally to the proximal end 866 of the recapture sheath 804. The Touhy-Borst valve 864 preferably is loosened and the deployment catheter 806 preferably is advanced distally relative to the recapture sheath 804 until the deployment handle 810 is within about 2 cm of the Touhy-Borst valve 864 of the recapture sheath 804. This causes the cage 300 to be advanced distally within the transseptal sheath 900 such that the recapture sheath 804 no longer covers the cage 300 or the flexible section 850. The Touhy-Borst valve 864 preferably is tightened to secure the deployment catheter 806 to fix relative movement between the deployment catheter 806 and recapture sheath 804.

Under fluoroscopy, the cage 300 preferably is advanced to the tip of the transseptal sheath 900 by distal movement of the deployment catheter 806. The distal hub 310 of the cage 300 preferably is aligned with a transseptal sheath 900 tip radiopaque marker 950, as illustrated in FIG. 13A. Under fluoroscopy, the sheath 900 position within the left atrium 104 preferably is confirmed with a distal contrast media injection. The distal end of the transseptal sheath 900 is positioned at, near, or inside of the ostium of the left atrial appendage 106, as illustrated in FIG. 15K.

The position of the cage 300 preferably is maintained by initially holding the deployment handle 810 stable. The transseptal sheath 900 preferably is withdrawn proximally until its tip radiopaque marker 950 is within about 1-2 mm of the septum 216 but still within the left atrium 104. This preferably exposes at least a portion of the cage 300, as shown in FIG. 15L.

Under fluoroscopy, the cage 300 preferably is expanded at least in part by rotating the control knob 814 clockwise. Rotating the control knob 814 preferably releases tension on the control line 888, preferably allowing the cage 300 to expand, as illustrated in FIG. 15M. At this point, the sheath 900 is advanced until the cage 300 abuts the vicinity of the left atrial appendage 106. The cage 300 is then deployed a little more. Sheath 900 advancement and cage 300 deployment and expansion is repeated until the cage 300 is fully deployed out of the sheath 900. The cage 300 preferably is self-expanding. After expansion, any tension on the left atrial appendage 106 or left atrium 104 preferably is removed by carefully retracting the deployment handle 810 under fluoroscopy until the radiopaque marker 858 on the axially movable core 808 moves proximally approximately 1-2 mm in the guide tube of the slider assembly 406. The position of the cage 300 relative the left atrial appendage 106 and left atrium 104 preferably is not altered because the axially movable core 808 preferably is coupled with the slider assembly 406, which allows for relative movement between the cage 300 and the axially movable core 808. The slider assembly 406 preferably allows for the distal portion of the axially movable core 808 to be slightly retracted proximally from the distal hub 310 of the cage 300, thereby removing any axial tension that may be acting on the cage 300 through the axially movable core 808. The radiopaque marker 858 preferably is about 1-2 mm proximal from the cage 300 distal hub 310, and the transseptal sheath 900 tip preferably is about 2-3 mm proximal from the implant proximal hub 308, thereby indicating a neutral position.

In one embodiment, the cage 300 is positioned within the left atrium 104 such that the barrier 500B covering its distal end 304 is aligned with the ostium of the left atrial appendage 106. In another embodiment, the cage 300 is positioned within the left atrium 104 such that the barrier 500A covering its proximal end 302 is aligned with a portion of the septum 216, such as a patent foramen ovale 944. In yet another embodiment, the cage 300 is positioned within the left atrium 104 such that the barrier 500B covering its distal end 304 is aligned with the ostium of the left atrial appendage 106 and the barrier 500A covering its proximal end 302 is aligned with a portion of the septum 216, such as a patent foramen ovale 944.

Under fluoroscopy, the expanded diameter of the cage 300 preferably is measured in at least two views to assess the position of the implant within the left atrium 104. The measured implant diameter preferably is compared to the maximum expanded diameter.

Preferably, the proximal and distal injection ports 818, 820 of the deployment handle 810, correlate with the proximal and distal contrast media injections. The proximal contrast media injections are delivered through the delivery catheter lumen 826 to a location proximal to the cage 300. The distal contrast media injections are delivered through the axially movable core 808 to a location distal to the cage 300. Proximal contrast media injections preferably are completed in two views. If the injection rate is insufficient, the recapture sheath injection port 870 may be used independently or in conjunction with the proximal injection port 818 to deliver fluid to a location proximal to the cage 300.

If satisfactory results are obtained, any transverse tension on the left atrial appendage 106 or left atrium 104 preferably is released by exposing the flexible segment 850 of the delivery system 800. The flexible catheter section 828 and the flexible core section 836 preferably are linearly co-located to cooperate as the flexible catheter section 828 of the delivery system 800, as described above. This preferably is accomplished by retracting the transseptal sheath 900 proximally approximately 2 cm to expose the flexible section 828. By exposing the flexible section 828, the flexible section 828 preferably will flex to allow the cage 300 to sit within the left atrium 104 free from transverse forces that may be created, for example, by contractions of the heart acting against the transseptal sheath 900 or deployment catheter 806.

Once the flexible section 828 is exposed, distal contrast media injections preferably are completed in at least two views to verify proper positioning of the cage 300. A flush of saline preferably is used as needed between injections to clear the contrast media from the left atrial appendage 106. Following the contrast media injections, the transseptal sheath 900 preferably is advanced distally to cover the flexible section 828.

Repositioning

If the cage 300 position or results are sub-optimal, the cage 300 preferably may be collapsed and repositioned in the left atrium 104. To do so, under fluoroscopy, the deployment handle 810 preferably is advanced distally to place the radiopaque marker 858 of the axially moveable core 808 at the distal hub 310 of the cage 300. The distal end of the transseptal sheath 900 preferably is aligned with the distal end of the flexible segment 850. The control knob 814 preferably is rotated until the cage 300 has been collapsed to approximately $\frac{1}{3}^{rd}$ or less of its expanded diameter. The tip of the transseptal sheath 900 can be withdrawn into the right atrium 114 during recapture to prevent excessive lengthening of the cage 300 within the left atrium 104 and potential tissue trauma. The control knob 814 preferably acts on the control line 888 to place tension on the proximal hub 308 of the cage 300, pulling the proximal hub 308 of the cage 300 proximally relative the distal hub 310 of the cage 300 to collapse the cage 300. The cage 300 preferably can be repositioned and re-expanded.

The stability of the cage 300 preferably is verified in several views. Stability tests preferably are preformed in the following manner. A contrast media filled syringe preferably is connected to the distal injection port 820 of the deployment handle 810. Under fluoroscopy, at least about a 10 mm gap between the tip of the transseptal sheath 900 and the proximal hub 308 of the cage 300 is preferably confirmed.

The stability of the cage 300 in the left atrium 104 preferably is evaluated using fluoroscopy and echocardiography. The recapture sheath Touhy-Borst valve 864 preferably is loosened. Then the deployment handle 810 preferably is alternately retracted and advanced about 5-10 mm while maintaining the position of the transseptal sheath 900 and simultaneously injecting contrast media through the distal injection port 820. This tests how well the implant is held within the left atrium 104.

If the implant stability tests are unacceptable, the cage 300 preferably may be collapsed and repositioned as described above. If repositioning the cage 300 does not achieve an acceptable result, the cage 300 preferably may be collapsed and recaptured as described further below.

The cage 300 preferably meets the following acceptance criteria, associated with the assessment techniques listed below, prior to being released. The assessment techniques to be evaluated preferably include 1) residual compression; 2) implant location; 3) anchor engagement; 4) seal quality; and 5) stability. For residual compression, the implant diameter, as measured by fluoroscopic imaging, preferably is less than the maximum expanded diameter of the cage 300. For implant location, the proximal sealing surface of the cage 300 preferably is positioned between the left atrial appendage 106 ostium and sources of thrombus formation (pectinates, secondary lobes, etc.) (preferably imaged in at least two views). For anchor engagement, the cage 300 frame 402 preferably is positioned within the left atrium 104 so as to engage a row of anchors or barbs 318 in a left atrial 104 wall (preferably imaged in at least two views). For seal quality, the contrast injections preferably show leakage rated no worse than mild (preferably defined as a flow of contrast media, well defined, and filling one-third of the left atrial appendage 106 during a proximal injection over a period of up to about five ventricular beats, preferably imaged in at least two views). For stability, there preferably is no migration or movement of the cage 300 relative to the left atrium 104 or septal defect as a result of the Stability Test, as described above.

Recapture and Retrieval

If cage 300 recapture is desired or necessary (e.g., because a different size cage 300 is necessary or desired), or if acceptable positioning or sealing cannot be achieved, the cage 300 preferably is fully collapsed as described above. Once the cage 300 is collapsed, the locking collar 872 of the peel away sheath 802 preferably is unlocked. The peel-away portion 874 of the peel-away sheath 802 preferably is split up to the reinforced section 876 and removed. The reinforced section 876 of the peel-away sheath 802 preferably is slid proximally to the hub of the recapture sheath 804. The Touhy-Borst valve 864 on the proximal end of the recapture sheath 804 preferably is slightly loosened to allow smooth movement of the recapture sheath 804 over deployment catheter 806 without allowing air to enter past the Touhy-Borst valve 864 seal. By removing the peel-away portion 874 of peel-away sheath 802, the recapture sheath 804 can now be advanced further distally relative to the transseptal sheath 900.

While holding the deployment catheter 806 and transseptal sheath 900 in place, the recapture sheath 804 preferably is advanced distally into the transseptal sheath 900 until a half marker band 868 on the recapture sheath 804 is aligned with a full marker band 950 on the transseptal sheath 900. This preferably exposes the recapture flares 860 outside the transseptal sheath 900.

The collapsed cage 300 preferably is retracted into the recapture sheath 804 by simultaneously pulling the deployment handle 810 and maintaining the position of the recapture sheath 804 until approximately half the cage 300 is seated in the recapture sheath 804. The Touhy-Borst valve 864 on the recapture sheath 804 preferably is tightened over the deployment catheter 806. The recapture sheath 804 and cage 300 preferably are retracted into the transseptal sheath 900 by pulling on the recapture sheath 804 while maintaining the position of the transseptal sheath 900, preferably maintaining left atrial access. The recapture flares 860 of the recapture sheath 804 preferably cover at least some of the anchor or barbs 318 on the cage 300 as the cage 300 is retracted proximally into the transseptal sheath 900.

De-Coupling

If the cage 300 position and function are acceptable, and cage 300 recapture is not necessary, the cage 300 preferably is released from the delivery system 800. Under fluoroscopy, the transseptal sheath 900 preferably is advanced to the proximal hub 308 of the cage 300 for support. The release knob 816 on the proximal end of the deployment handle 810 preferably is rotated to release the cage 300. Rotating the release knob 816 preferably causes a mating surface 856, such as a threaded portion, of the distal shaft 834 of the axially movable core 808 to rotate with respect to the slider assembly 406 such that the mating surface 856 preferably is decoupled from the slider assembly 406. Under fluoroscopy, after the axially movable core 808 is decoupled from the cage 300, the release knob 816 preferably is retracted until the distal shaft 834 of the axially movable core 808 is at least about 2 cm within the transseptal sheath 900.

Under fluoroscopy, while assuring that transseptal access is maintained, the delivery system 800 preferably is retracted and removed through the transseptal sheath 900. Under fluoroscopy, the transseptal sheath 900 position preferably is verified to be approximately 1 cm away from the face of the cage 300. Contrast injections, fluoroscopy and/or echocardiography preferably may be used to confirm proper positioning and delivery of the cage 300 and position with respect to the left atrial appendage 106 and septum 216. The transseptal sheath 900 preferably is withdrawn, as illustrated in FIG. 15N.

When the cage 300 is positioned within the left atrium 104 as illustrated in FIG. 15N, a continuous light pressure is applied to the septum primum 948 from the left atrial 104 side. The barrier 500A on the proximal face 502 of the cage 300 generally includes an ePTFE lamination or other structure that promotes neointimal growth and endothelialization. As ingrowth and endothelialization occur, a naturally formed barrier to seal, close, or patch a defect in the septum 216 is achieved. The cage 300 provides a frame or scaffolding to hold the barrier 500B in place against the septum 216 and across and/or inside of the left atrial appendage 106, as described in greater detail above.

One advantage of the intracardiac cage 300 is that gross stretching or distension of the patent foramen ovale 944 opening do not occur, either for sizing, or because of oblique attachment. Although the intracardiac cage 300 has been primarily described with respect to implantation within the left atrium 104, it should be understood by those of skill in the art that the same or equivalent structures can be used within the right atrium of the heart to provide a barrier 500 against the septum secundum 946 and/or the ostium of the right atrial appendage 116. In addition, the same or similar structures may be used to provide a barrier 500 against any septal defect, whether in the interatrial septum or the interventricular septum. For example, the present invention may be used to provide a barrier to seal off, block, or filter an atrial septal defect (ASD), a ventricular septal defect (VSD), a patent foramen ovale (PFO), or a patent ductus arteriosis (PDA).

Although throughout this application the term cage has been used, those of skill in the art should understand that the terms implant and occlusion device may be used as well to describe identical or equivalent structures. One of ordinary skill in the art will appreciate that all of the disclosures herein are applicable to a wide variety of structures that include both cages and implants that may or may not also be occlusion devices. Routine experimentation will demonstrate those limited circumstances under which certain disclosures and combinations thereof are not beneficial.

What is claimed is:

1. A method of preventing ingress of material into the left atrium of a heart, comprising:
   providing a delivery sheath having a sheath proximal end, a sheath distal end, and said sheath having a lumen extending therethrough;
   said delivery sheath extending to the right atrium of the heart atrium;
   advancing the sheath distal end through an opening between the right atrium and the left atrium;
   providing an expandable cage, having a proximal end, a distal end, a plurality of supports extending therebetween, a first membrane provided at the proximal end, and a second membrane provided at the distal end, the expandable cage having a collapsed configuration to be received within the lumen of the delivery sheath, and an expanded configuration for deployment within the heart;
   said expandable cage being extensible from a first shorter configuration to a second longer configuration to accommodate motion on the left atrium of the heart;
   delivering the expandable cage to the left atrium of the heart through the delivery sheath; and
   expanding the expandable cage within the left atrium, the expandable cage when expanded positions the second membrane at the ostium of the left atrial appendage, wherein the second membrane prevents passage of embolic material from the left atrial appendage into the left atrium, and positioning the first membrane at an opening between the left atrium and a right atrium of the heart, where the first membrane substantially prevents passage of blood between the atria.

2. The method of claim 1, wherein the opening is a natural opening.

3. The method of claim 1, wherein the opening is formed by piercing the atrial septum.

4. The method of claim 1, wherein the opening is a patent foramen ovale.

5. The method of claim 1, wherein the cage is a septal defect.

6. The method of claim 1, wherein the cage is self expanding.

7. The method of claim 1, wherein the cage is expanded by retracting the delivery sheath proximally.

8. The method of claim 1, wherein the delivering step comprises pulling the delivery sheath proximally with respect to the expandable cage prior to said expanding step.

9. The method of claim 1, wherein the delivering step comprises pushing the expandable cage past the sheath distal end prior to said expanding step.

10. The method of claim 1, wherein said delivering the expandable cage comprises positioning the cage distal of the distal end prior to said expanding step.

11. The method of claim 1, further comprising verifying the position of the expandable cage within the left atrium, wherein said verifying is performed prior to said expanding step.

12. The method of claim 1, further comprising repositioning said cage within the left atrium.

13. The method of claim 1, further comprising retrieving said cage from the left atrium.

* * * * *